(12) United States Patent
Foley

(10) Patent No.: US 12,098,120 B2
(45) Date of Patent: Sep. 24, 2024

(54) *HUMULUS* SPECIES AS INDUSTRIAL CHEMICAL FEEDSTOCKS

(71) Applicant: P2 SCIENCE, INC., Woodbridge, CT (US)

(72) Inventor: Patrick Foley, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/820,861

(22) Filed: Aug. 18, 2022

(65) Prior Publication Data

US 2023/0138884 A1 May 4, 2023

Related U.S. Application Data

(60) Provisional application No. 63/234,294, filed on Aug. 18, 2021.

(51) Int. Cl.
| | | |
|---|---|---|
| *C07C 35/06* | (2006.01) | |
| *C07C 13/10* | (2006.01) | |
| *C07C 13/18* | (2006.01) | |
| *C07C 35/08* | (2006.01) | |
| *C07C 35/14* | (2006.01) | |
| *C07C 49/297* | (2006.01) | |
| *C07C 49/303* | (2006.01) | |
| *C07C 49/537* | (2006.01) | |
| *C07C 49/703* | (2006.01) | |

(52) U.S. Cl.
CPC .............. *C07C 35/06* (2013.01); *C07C 13/10* (2013.01); *C07C 13/18* (2013.01); *C07C 35/14* (2013.01); *C07C 49/297* (2013.01); *C07C 49/303* (2013.01); *C07C 49/537* (2013.01); *C07C 49/703* (2013.01); *C07C 2601/08* (2017.05); *C07C 2601/10* (2017.05); *C07C 2601/14* (2017.05); *C07C 2601/16* (2017.05)

(58) Field of Classification Search
CPC ......... C07C 35/06; C07C 35/08; C07C 35/14; C07C 49/297; C07C 49/303; C07C 49/537; C07C 49/703
See application file for complete search history.

(56) References Cited

U.S. PATENT DOCUMENTS 8,871,978 B2 * 10/2014 Ting ..................... C07C 49/713
564/303

OTHER PUBLICATIONS

Carson, J.F., The Hydrogenation of Lupulone and Humulone. Western Regional Research Laboratory, vol. 73, 1850-1851. (Year: 1950).*
Knez Hrnčič et al., "Hop Compounds: Extraction Techniques, Chemical Analyses, Antioxidative, Antimicrobial, and Anticarcinogenic Effects," Nutrients, vol. 11, No. 257, 37 pages, (2019).
Stevens, R., "The Chemistry of Hop Constituents," Chem Rev., vol. 67, No. 1, p. 19-71, (1967).

* cited by examiner

*Primary Examiner* — Sikarl A Witherspoon
(74) *Attorney, Agent, or Firm* — Hoxie & Associates LLC

(57) ABSTRACT

The present disclosure is directed to novel derivatives of naturally occurring humulones and lupulones, methods of making them, compositions comprising them, and methods for using them.

22 Claims, No Drawings

HUMULUS SPECIES AS INDUSTRIAL CHEMICAL FEEDSTOCKS

CROSS-REFERENCE TO RELATED APPLICATIONS

This application is a U.S. nonprovisional application filed under 35 U.S.C. § 111(a), which claims priority to U.S. provisional application 63/234,294, filed on Aug. 18, 2021, the contents of which are hereby incorporated by reference in its entirety.

FIELD OF INVENTION

The present disclosure is directed to novel derivatives of naturally occurring humulones and lupulones, methods of making them, compositions comprising them, and methods for using them.

BACKGROUND

Natural products are a sought-after source of industrially useful chemicals because of their biorenewability. Industrial chemicals derived from natural gas, petroleum, and other non-renewable sources are increasingly frowned upon because of the effect on the environment from their extraction as well as due to their limited nature and increasing costs associated with extraction. In contrast, the use of naturally occurring biological feedstocks effectively provides a solar-energy empowered source of chemical precursors and fuels for industry. Plants which are rapidly growing and provide high concentrations of useful biochemical feedstocks are particularly important.

For example, terpenes and terpene derivatives are a diverse, commercially sought after, and industrially important classes of natural products. Terpenes occur in all organisms and are particularly prevalent in plants, from which they are industrially isolated. The ready commercial access and low-cost of terpenes continually drives innovation into their chemical derivatization which find use in polymer science, the flavor & fragrance industry, the cosmetic industry, the pharmaceutical industry, and as surfactants, plastic additives, and other industrial uses.

However, there remains a need for new sources of natural chemical feedstocks that can supplement or replace terpenes and other currently known biofeedstocks.

*Humulus* plants, commonly known as hops, are a well-known genus of flowering plants in the family Cannabaceae. Hops are traditionally the female flowers of the species *Humulus lupulus*. Other recognized species within the family are *Humulus japonicus, Humulus americanus, Humulus cordiofolius, Humulus neomexicanus*, and *Humulus yunnanensis*. Hops is most well known as the primary flavoring agent, along with wort, in beer-making. A large variety of cultivars have been produced for beer-making, which differ in the flavors and aromas they impart to beer. Hops is also used medicinally to prepare infusion of hop, tincture of hop, and extract of hop.

Hops extracts contain a variety of organic compounds, and extracts from hops plants can be divided into soft resins and hard resins. Hard resins consist primarily of polyphenols, flavonols, flavonoids and phenolic glycosides. Soft resins consist of the bitter acids. The bitter taste of that hops imports to beer is primarily the result of so-called bitter acids, which are divided into alpha-acids (the humulones) and beta-acids (the lupulones). Hops also contains essential oils, such as linalool, pinene, myrcene, and humulenes. See, e.g., Bren et al., *Nutrients,* 2019, 11, 257 (doi:10.3390/nu11020257).

Some of the more important humulones and lupulones include the following compounds:

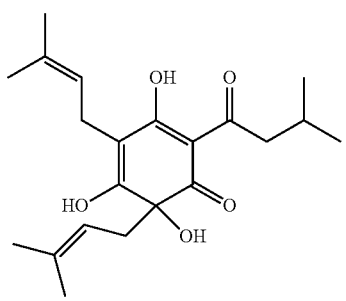

Humulone

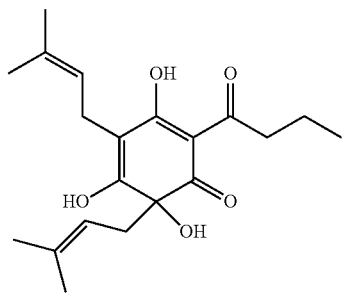

Cohumulone

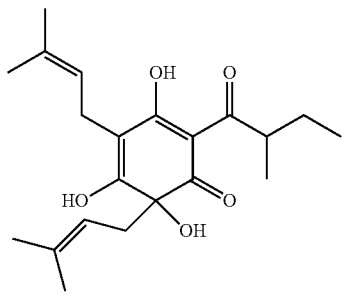

Adhumulone

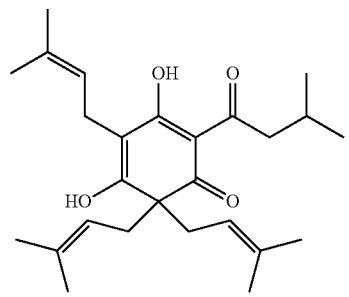

Lupulone

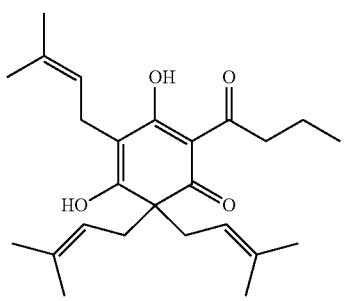

Colupulone

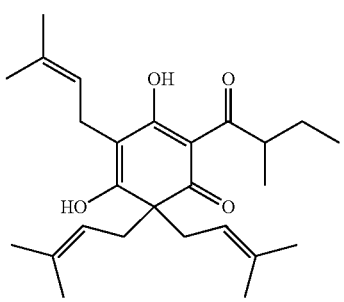

Adlupulone

Humulones are also known to undergo thermal isomerization, such as by boiling during beer brewing, to form the five-membered ring isohumulones. For example:

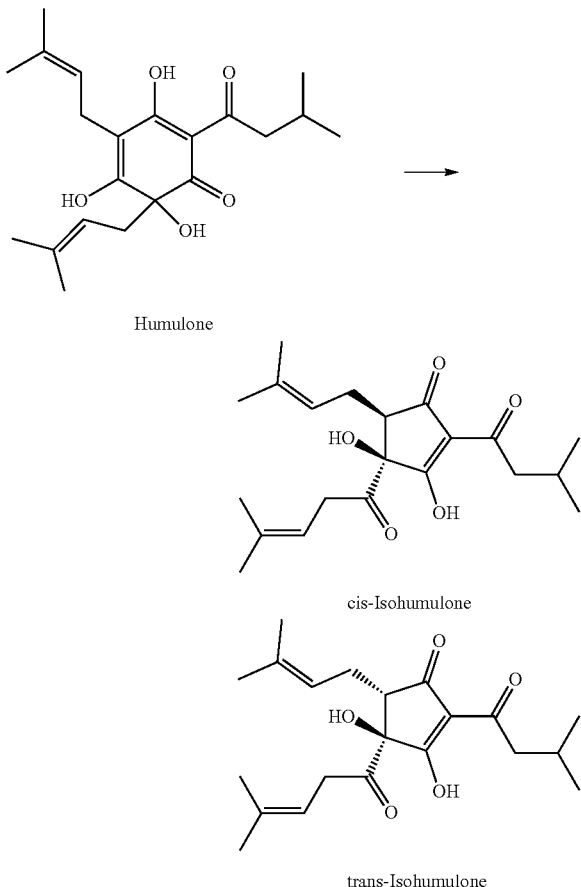

Humulone cis-Isohumulone trans-Isohumulone

More than 100,000 tons of hops is grown annually across the world, primarily for the use in making beer. Depending on the cultivar, hops can have from 5 to 20% by weight of alpha-acids and beta-acids.

There exists already a large significant chemical industry based on renewable, biologically derived source materials. For example, numerous lubricants, solvents (e.g., vegetable oils), and fibrous materials are derived from wood, rags, and grasses. In addition, ethanol, sugars and starches are extracted from crops such as corn. However, many of these crops have the drawbacks, such as, long periods of growth to maturity, or competing use as human or animal foodstuffs.

There remains a need for a new, versatile, cheap, rapidly growing biological sources of industrial chemical feedstocks.

BRIEF SUMMARY OF THE INVENTION

The present disclosure provides novel derivatives of naturally occurring humulones and lupulones, which can be used as chemical feedstocks for the production of novel large-volume industrial chemicals, such as, surfactants, emollients, lubricants, defoamers, adjuvants, fuels, and other ingredients especially useful in personal care compositions (e.g., soaps, hair care products), cosmetic compositions (e.g., sunscreens), household cleaning compositions (e.g., cleaning solutions and laundry detergents), crop care compositions (e.g., insecticides and herbicides), as well as polymer precursors and additives for plastics, paints, and coatings.

In a second aspect, the present disclosure provides a method of preparing such compounds.

In a third aspect, the present disclosure provides compositions and products comprising such compounds.

DETAILED DESCRIPTION OF THE INVENTION

In a first aspect, the present disclosure provides a compound (Compound 1) which is a hydrogenated derivative of a humulone, lupulone or isohumulone. As used herein, the term "hydrogenated derivative" means that at least one exocyclic double bond and/or at least the central cyclohexa-2,4-dien-1-one ring (or cyclopenta-2-ene-1-one ring) of the humulone, lupulone, or isohumulone, are hydrogenated, for example, to form a saturated exocyclic moiety and/or a saturated or partially saturated cyclohexane or cyclopentane ring (e.g., a cyclohexanone, cyclohexanol, cyclopentanone, cyclopentanol, cyclohexanone or cyclohexanol ring).

In some embodiments of the first aspect, the compound is a hydrogenated derivative of humulone, cohumulone, or adhumulone. In other embodiments of the first aspect, the compound is a hydrogenated derivative of lupulone, colupulone, or adlupulone. In some embodiments the compound is hydrogenated and deoxygenated.

In further embodiments of the first aspect, the present disclosure provides as follows:

1.1 Compound 1, wherein the compound has a structure selected from the following:

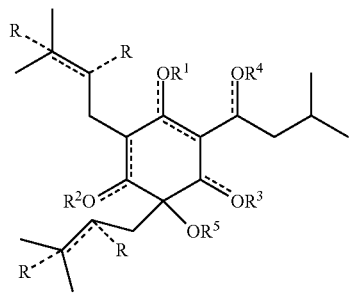
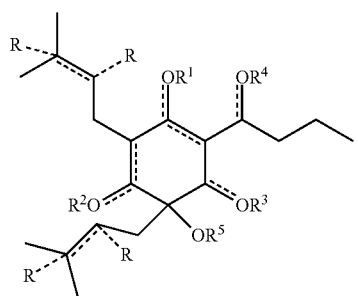
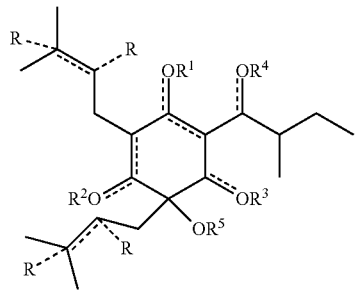

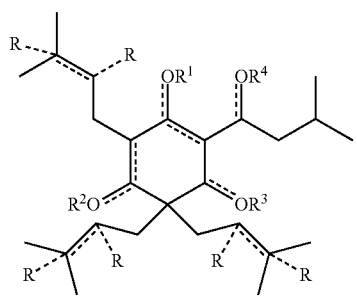
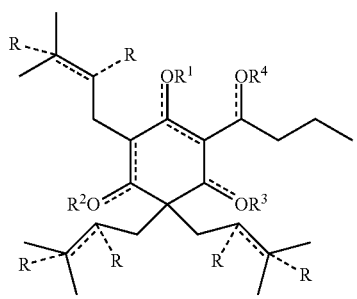
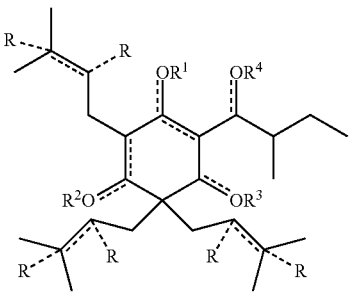

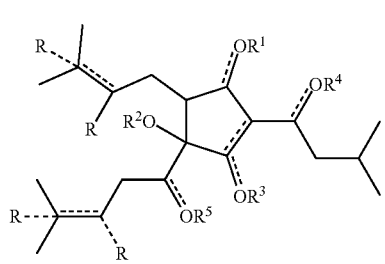
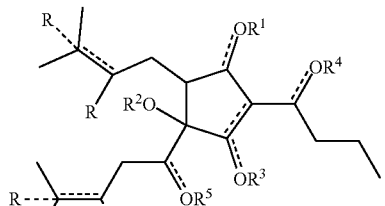
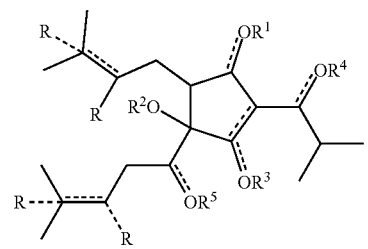

wherein:
- each R is independently selected from H, OH, $OC_{1-21}$ alkyl, and $-OC(O)-C_{1-21}$ alkyl, or any R is absent;
- $R^1$, $R^2$, $R^3$, $R^4$, and $R^5$, are each independently selected from H, $C_{1-21}$ alkyl, $-C(O)-C_{1-21}$ alkyl, $C_{2-21}$ alkenyl, $-C(O)-C_{2-21}$ alkenyl, $C_{3-7}$cycloalkyl, $-C(O)-C_{3-7}$cycloalkyl, $C_{1-6}$ haloalkyl, $-C(O)-C_{1-6}$ haloalkyl, $(CH_2CH_2O)nCH_2CH_2OH$, $(CH_2CH(CH_3)O)nCH_2CH(CH_3)OH$, $C_{1-21}$ alkyl-OH, $-C(O)-C_{1-21}$ alkyl-OH, $C_{1-21}$ alkyl-C(O)-OC_{1-6}$ alkyl, $C(O)-C_{1-21}$ alkyl-C(O)-OC_{1-6}$ alkyl, $C_{1-21}$ alkyl-COOH, $-C(O)-C_{1-21}$ alkyl-COOH, $-P(O)(OC_{1-21}$ alkyl)(OC_{1-21}$ alkyl), $-SO_2OC_{1-21}$ alkyl, $-SO_2C_{1-21}$ alkyl, $C_{1-21}$ alkyl-P(O)(OC_{1-6}$ alkyl)(OC_{1-6}$ alkyl), $-C(O)-C_{1-21}$ alkyl-P(O)(OC_{1-6}$ alkyl)(OC_{1-6}$ alkyl), $C_{1-21}$ alkyl-P(O)(OH)(OC_{1-6}$ alkyl), $-C(O)-C_{1-21}$ alkyl-P(O)(OH)(OC_{1-6}$ alkyl), $C_{1-21}$ alkyl-P(O)(OH)_2$, $-C(O)-C_{1-21}$ alkyl-P(O)(OH)_2$, $C_{1-21}$ alkyl-SO_2OC_{1-6}$ alkyl), $-C(O)-C_{1-21}$ alkyl-SO_2OC_{1-6}$ alkyl, $C_{1-21}$ alkyl-SO_3H$, and $-C(O)-C_{1-21}$ alkyl-SO_3H$; or any of $R^1$, $R^2$, $R^3$, or $R^4$, is absent; and wherein each n is independently an integer selected from 0 to 20;
- wherein each "═══" is either a single bond or a double bond, and wherein each "- - -" is either a single bond or is absent; and
- provided that the bonds "═══" and "- - -" are selected such that all carbon atoms and oxygen atoms to which these bonds are attached have a total of four attached bonds inclusive of single and double bonds (e.g., if $R^1$, $R^2$, $R^3$, or $R^4$ is absent, then the bond attached to the respective oxygen atom is a double bond).

1.2 Compound 1.1, wherein the compound has a structure selected from the following:

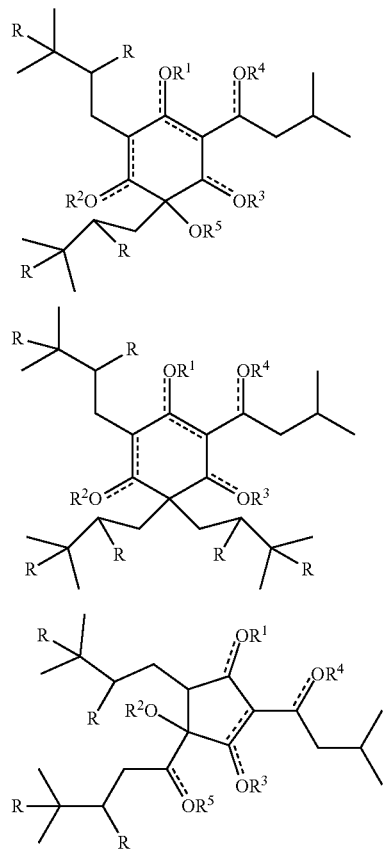
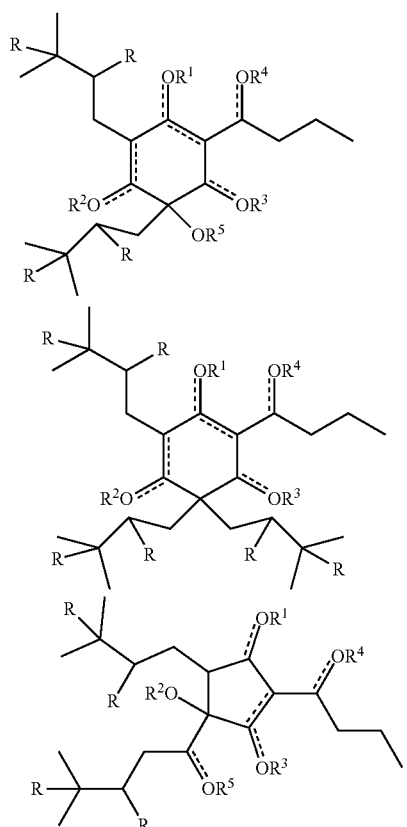
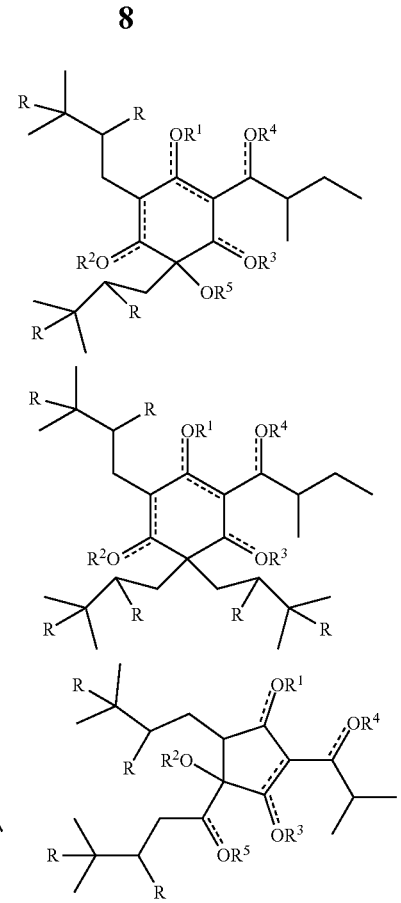
wherein each R is independently H or OH, and $R^1$, $R^2$, $R^3$, $R^4$, and $R^5$ are each as defined for compound 1.1.
1.3 Compound 1.1, wherein the compound has a structure selected from the following
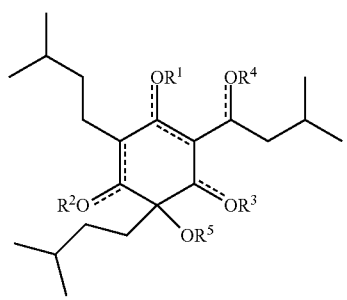
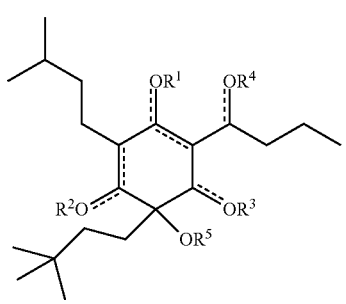
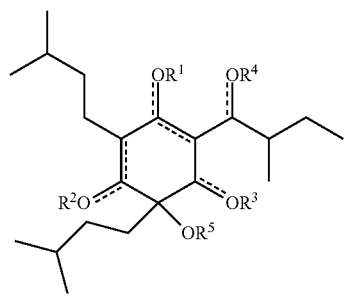
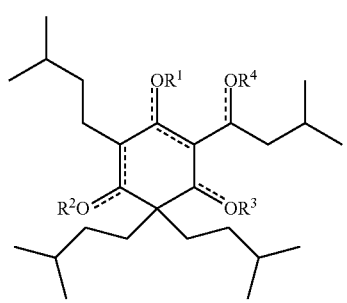
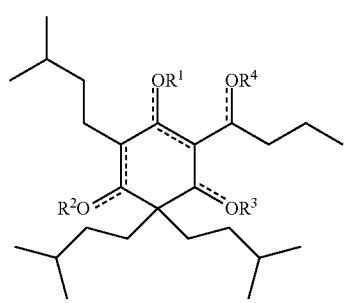
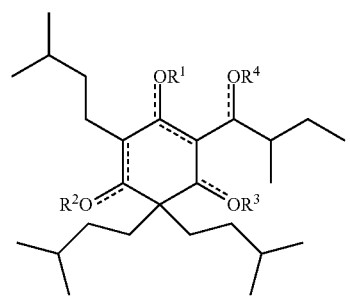

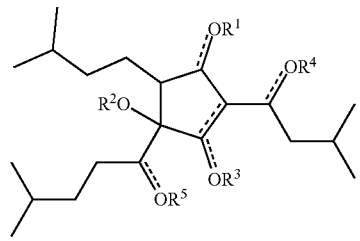 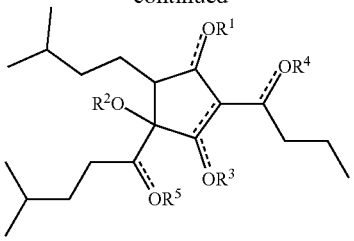 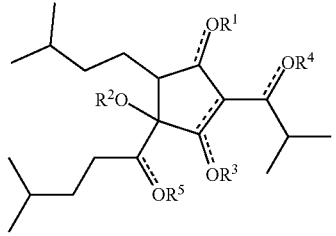
wherein $R^1$, $R^2$, $R^3$, $R^4$, and $R^5$ are each as defined for compound 1.1.
1.4 Compound 1.1, wherein the compound has a structure selected from the following
wherein $R^1$, $R^2$, $R^3$, $R^4$, and $R^5$ are each as defined for compound 1.1.
1.5 Compound 1.1, wherein the compound has a structure selected from the following:
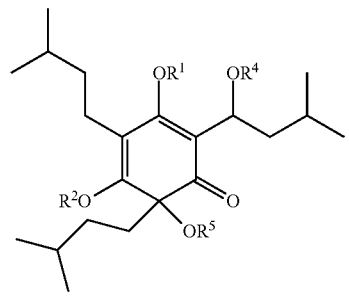 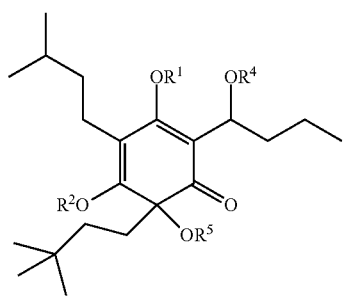 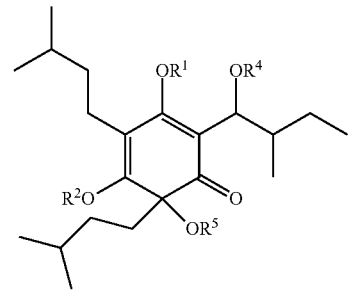
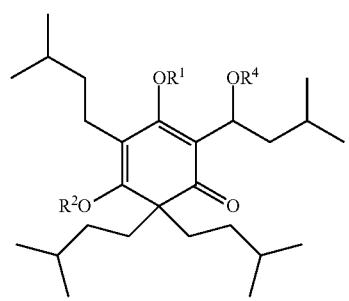 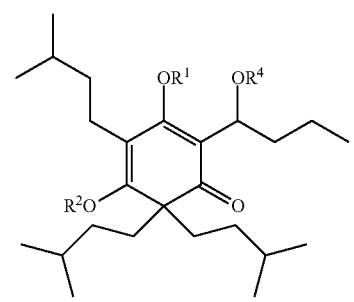 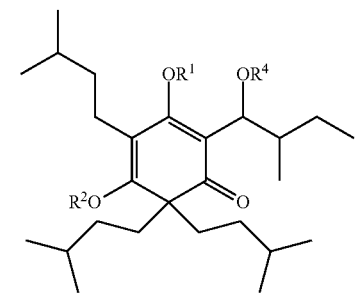
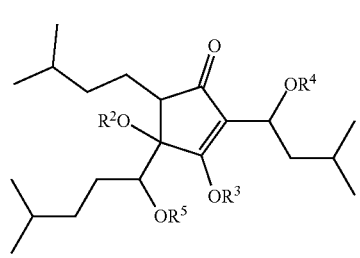 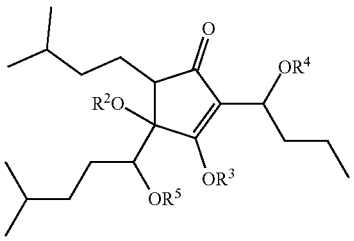 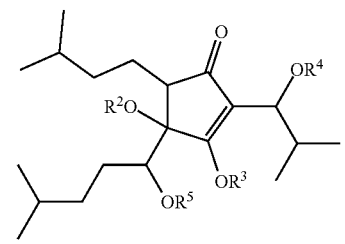

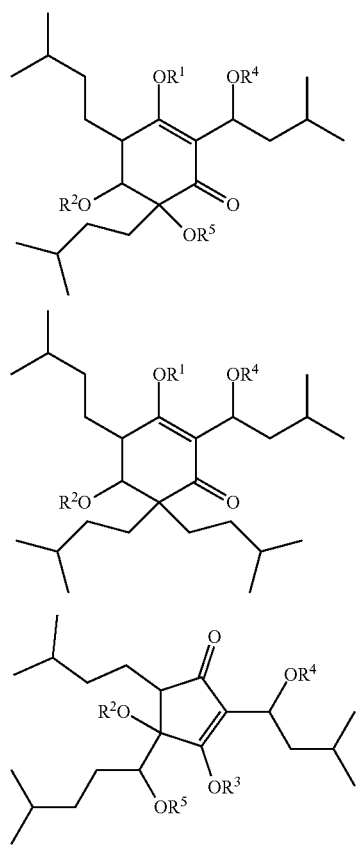
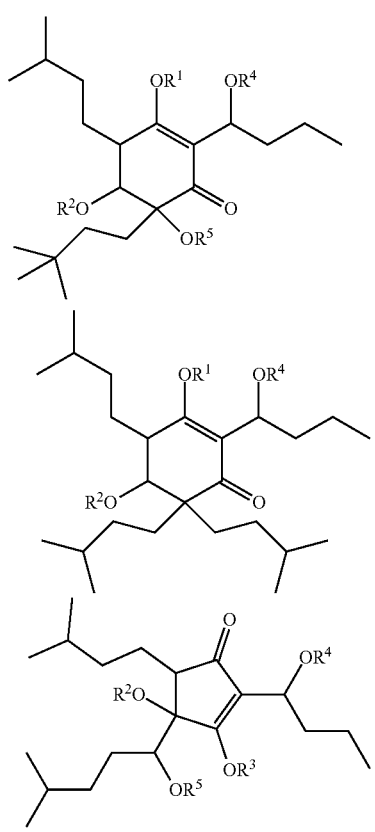
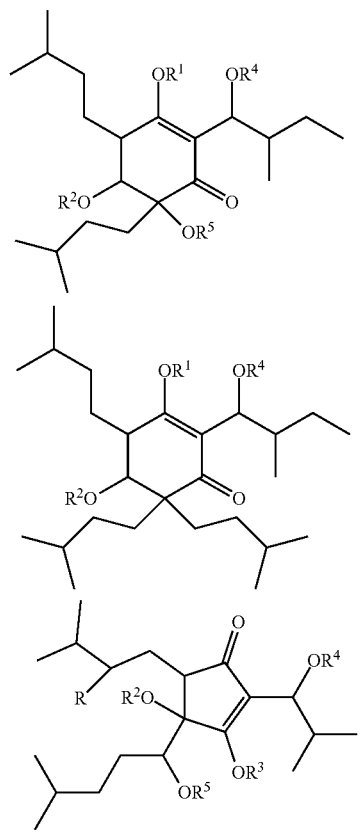
wherein $R^1$, $R^2$, $R^3$, $R^4$, and $R^5$ are each as defined for compound 1.1.
1.6 Compound 1.1, wherein the compound has a structure selected from the following:
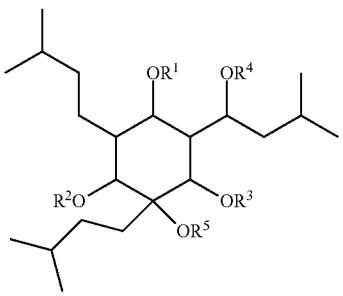
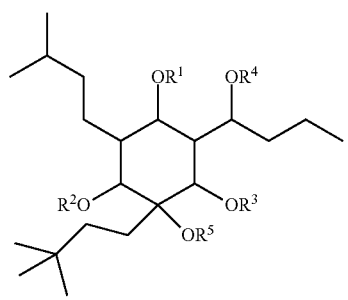
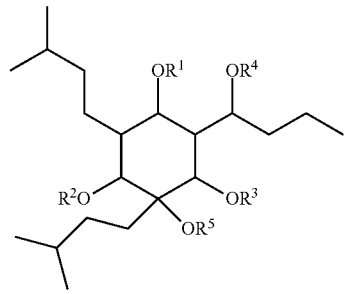
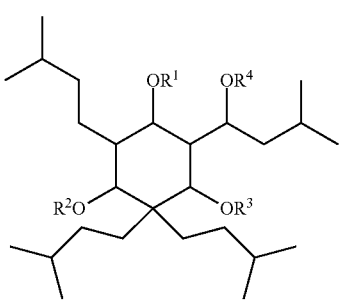
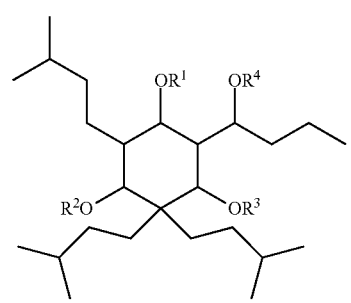
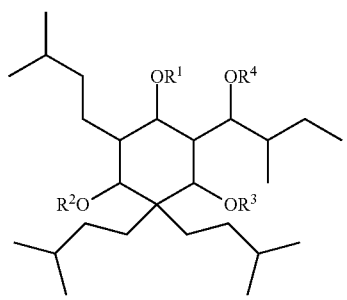

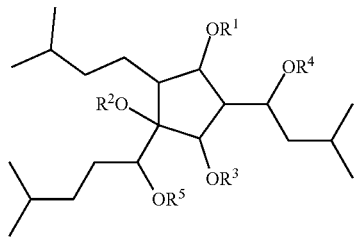 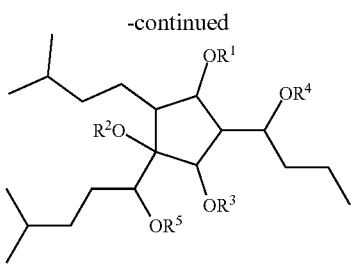 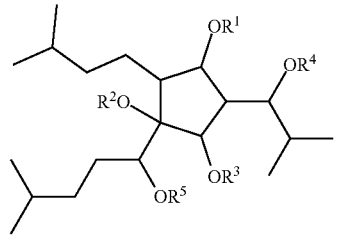

wherein $R^1$, $R^2$, $R^3$, $R^4$, and $R^5$ are each as defined for compound 1.1.

1.7 Any combination of compounds selected from the compounds of 1.1-1.6.

1.8 Any of compounds 1.1-1.7, wherein each pair of adjacent groups R is OH, $OC_{1-21}$alkyl, or —OC(O)—$C_{1-21}$ alkyl.

1.9 Any of compounds 1.1-1.7, wherein each pair of adjacent groups R consist of one H and one group selected from OH, $OC_{1-21}$alkyl, and —OC(O)—$C_{1-21}$ alkyl.

1.10 Any of compounds 1.1-1.7, wherein each group R is H.

1.11 Any of compounds 1.1-1.10, wherein $R^1$, $R^2$, and $R^5$ are each H, and $R^3$ and $R^4$ are absent (e.g., for a humulone or lupulone core); or wherein $R^2$ and $R^3$ are each H, and $R^1$, $R^4$, and $R^5$ are absent (e.g., for an isohumulone core).

1.12 Any of compounds 1.1-1.10, wherein $R^1$, $R^2$, $R^5$ and $R^3$ are each H (e.g., for a humulone or lupulone core); or wherein $R^1$, $R^2$, $R^3$, $R^4$, and $R^5$ are each H (e.g., for an isohumulone core).

1.13 Any of compounds 1.1-1.10, wherein $R^1$, $R^2$, and $R^5$ are each $C_{1-21}$ alkyl, —C(O)—$C_{1-21}$ alkyl, $C_{2-21}$ alkenyl, or —C(O)—$C_{2-21}$ alkenyl, and $R^3$ is absent.

1.14 Any of compounds 1.1-1.10, wherein $R^1$, $R^2$, and $R^5$ and $R^3$ are each $C_{1-21}$alkyl, —C(O)—$C_{1-21}$alkyl, $C_{2-21}$ alkenyl, or —C(O)—$C_{2-21}$ alkenyl.

1.15 Any of compounds 1.1-1.10, wherein $R^1$, $R^2$, and $R^5$ are each $CH_3$ or —C(O)$CH_3$.

1.16 Any of compounds 1.1-1.10, wherein $R^1$, $R^2$, and $R^5$ and $R^3$ are each $CH_3$ or —C(O)$CH_3$.

1.17 Any of compounds 1.1-1.16, wherein $R^4$ is absent.

1.18 Any of compounds 1.1-1.16, wherein $R^4$ is H.

1.19 Any of compounds 1.1-1.16, wherein $R^4$ is $C_{1-21}$ alkyl, —C(O)—$C_{1-21}$ alkyl, $C_{2-21}$alkenyl, or —C(O)—$C_{2-21}$ alkenyl.

1.20 Any of compounds 1.1-1.19, wherein $R^3$ or $R^5$ or both is $(CH_2CH_2O)nCH_2CH_2OH$ or $(CH_2CH(CH_3)O)nCH_2CH(CH_3)OH$, wherein n is an integer from 0 to 20;

1.21 Any of compounds 1.1-1.19, wherein $R^3$ or $R^5$ or both is $C_{1-21}$alkyl-OH or —C(O)—$C_{1-21}$alkyl-OH.

1.22 Any of compounds 1.1-1.19, wherein $R^3$ or $R^5$ or both is $C_{1-21}$alkyl-COOH or —C(O)—$C_{1-21}$alkyl-COOH.

1.23 Any of compounds 1.1-1.19, wherein $R^3$ or $R^5$ or both is $C_{1-21}$alkyl-C(O)—$OC_{1-6}$alkyl or C(O)—$C_{1-21}$ alkyl-C(O)—$OC_{1-6}$ alkyl.

1.24 Any of compounds 1.1-1.19, wherein $R^3$ or $R^5$ or both is $C_{1-21}$alkyl-P(O)($OC_{1-6}$alkyl)($OC_{1-6}$ alkyl), —C(O)—$C_{1-21}$alkyl-P(O)($OC_{1-6}$ alkyl)($OC_{1-6}$ alkyl), $C_{1-21}$alkyl-P(O)(OH)($OC_{1-6}$ alkyl), —C(O)—$C_{1-21}$ alkyl-P(O)(OH)($OC_{1-6}$ alkyl), $C_{1-21}$ alkyl-P(O)(OH)$_2$, or —C(O)—$C_{1-21}$ alkyl-P(O)(OH)$_2$.

1.25 Any of compounds 1.1-1.19, wherein $R^3$ or $R^5$ or both is $C_{1-21}$ alkyl-$SO_2OC_{1-6}$alkyl), —C(O)—$C_{1-21}$alkyl-$SO_2OC_{1-6}$ alkyl, $C_{1-21}$ alkyl-$SO_3H$, or —C(O)—$C_{1-21}$ alkyl-$SO_3H$.

1.26 Compound 1.1, wherein the compound has a structure selected from the

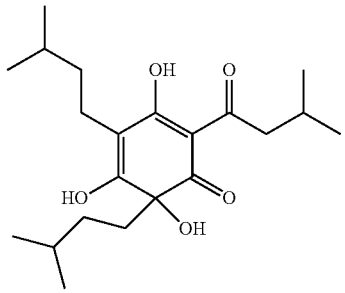 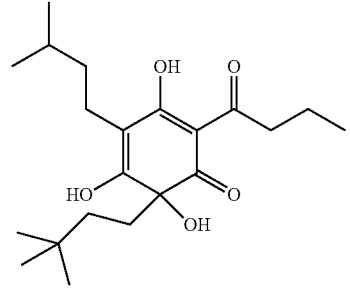 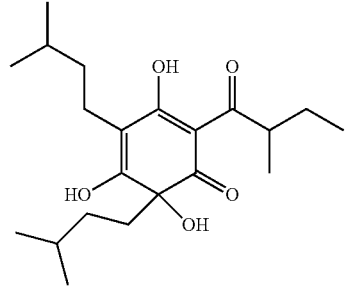

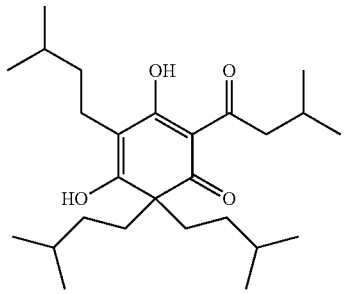 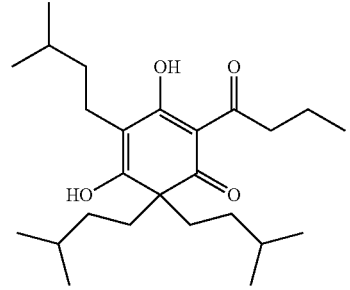 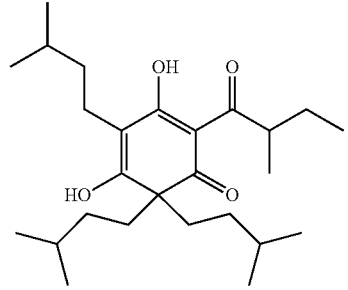

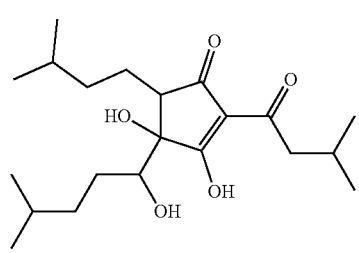 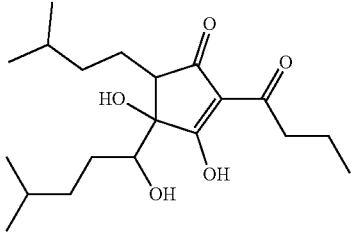 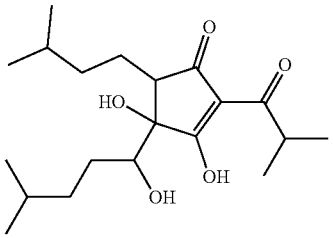
1.27 Compound 1.1, wherein the compound has a structure selected from the following
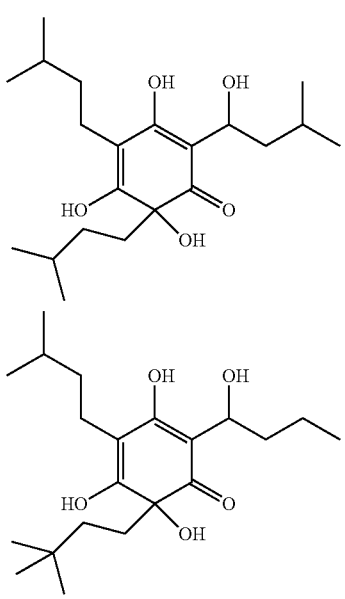
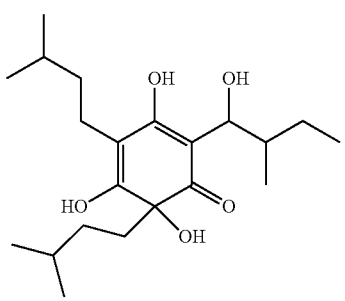
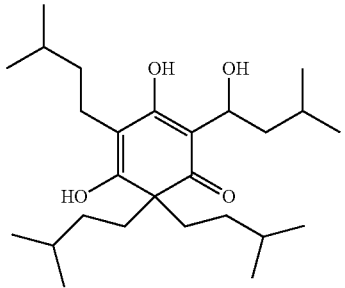
-continued
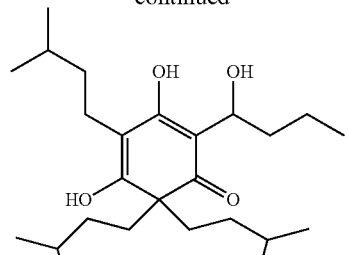
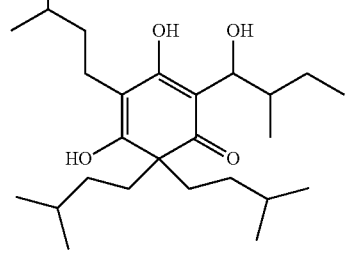
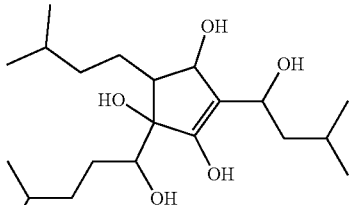
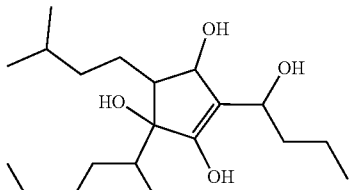
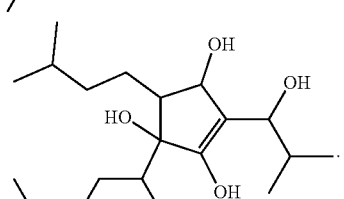
1.28 Compound 1.1, wherein the compound has a structure selected from the following:

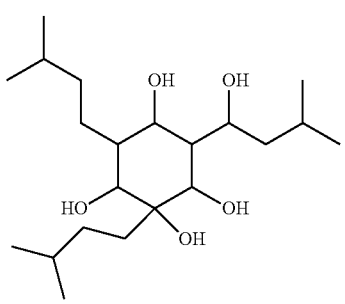
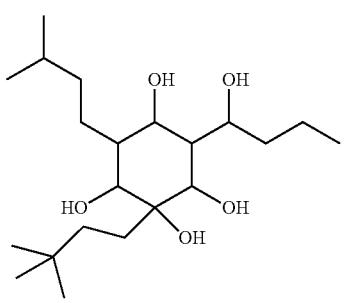
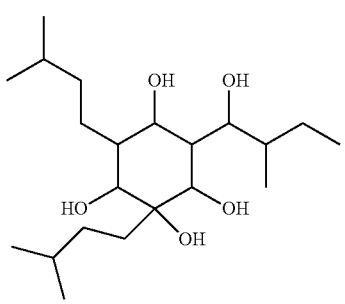
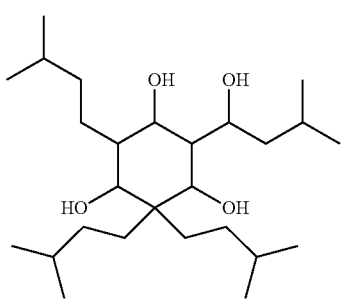
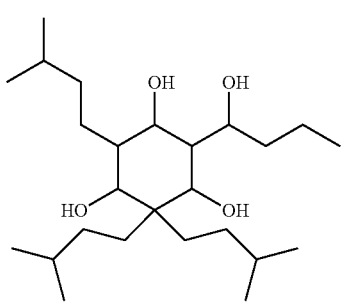
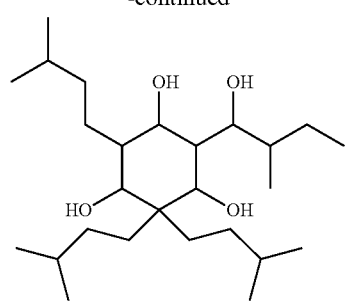
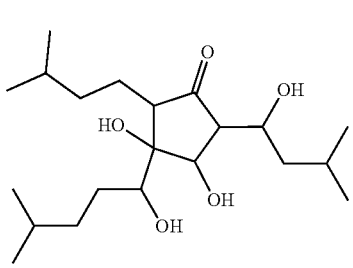
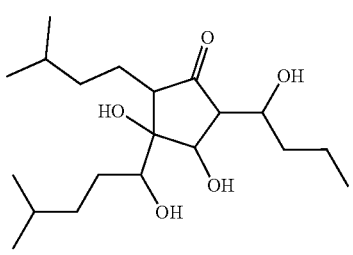
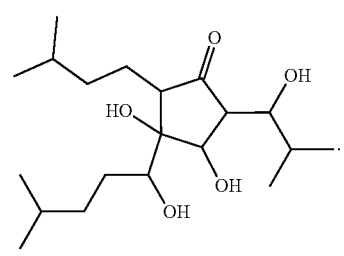
1.29 Compound 1.1, wherein the compound has a structure selected from the following:
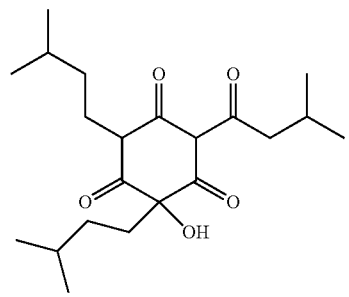

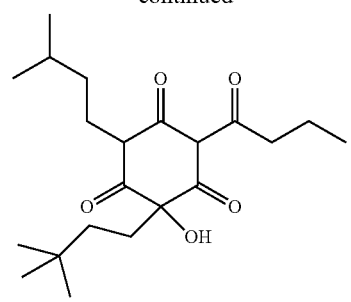
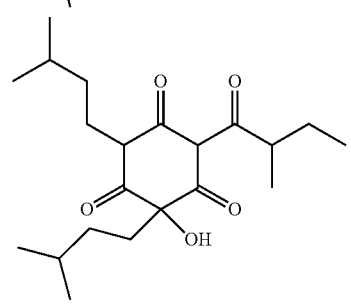
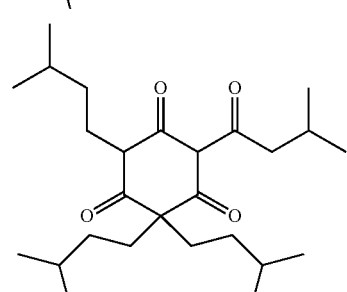
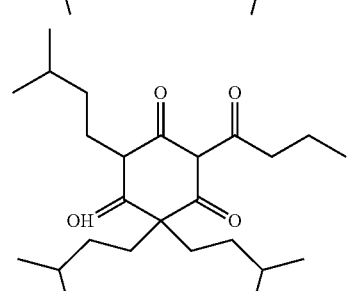
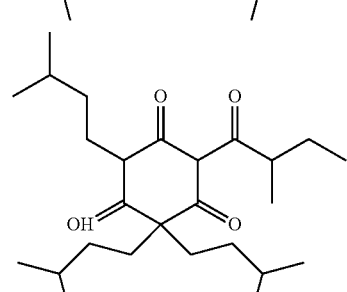
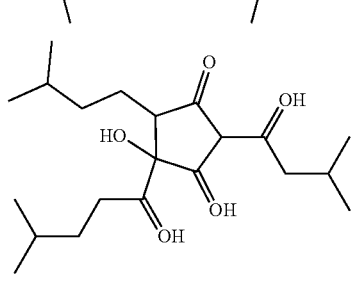
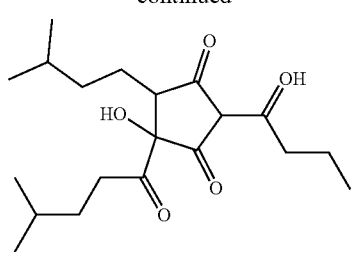
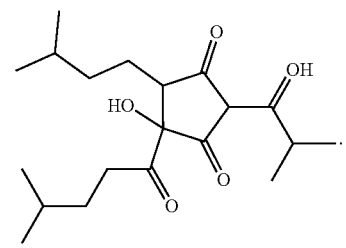
1.30 Compound 1.1, wherein the compound has a structure selected from the following:
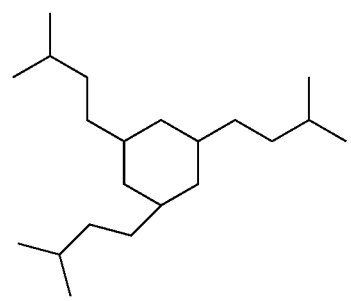
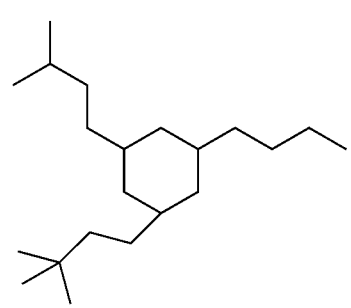
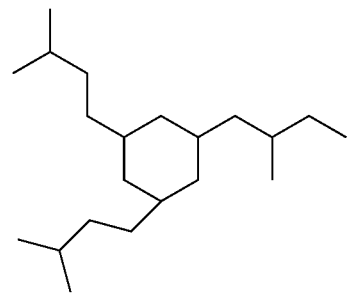

-continued

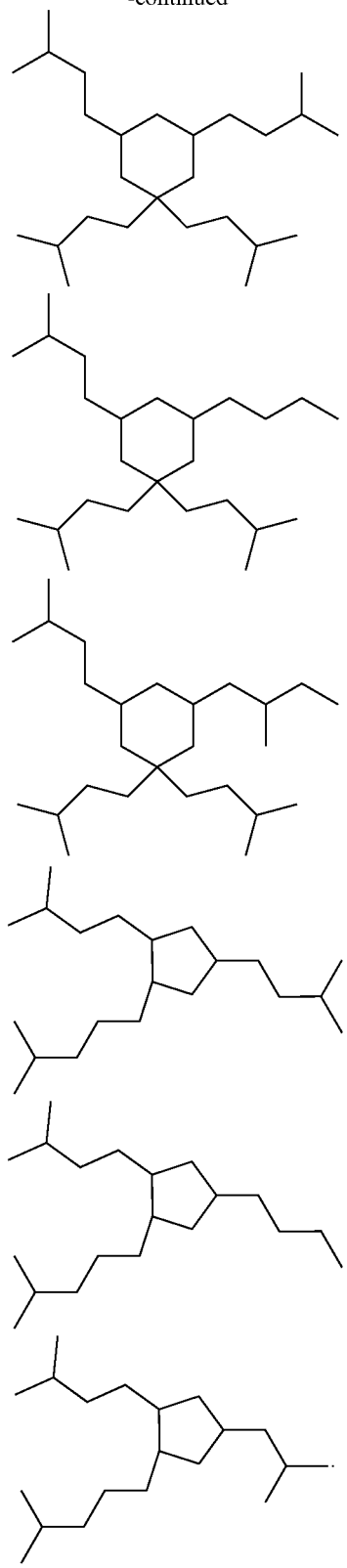

1.31 Any compounds 1.1-1.30, wherein the compound is a racemic mixture of all possible enantiomers and diastereomers (i.e., the stereoisomers have not been resolved).

1.32 Any of compounds 1.1-1.30, wherein the compound has been resolved into any single pair of enantiomers (i.e., a racemate), free or substantially free of any diastereomeric isomers.

1.33 Any of compounds 1.1-1.30, wherein the compound has been resolved into a single enantiomer, e.g., having an enantiomeric excess (e.e.) of at least 75%, or of at least 80%, or of at least 85%, or of at least 90%, or at least 95% or at least 98%.

1.34 A polymeric derivative of any one of compounds 1.1-1.33, such as a polyester, polyimide, polyamide, polycarbonate, polycarbamate, or polyurethane polymer 1.35 A polyester derivative of any one of compounds 1.1-1.33 wherein the compound comprises at least two hydroxy groups and the polymer is a heteropolymer formed
between such compound and an aliphatic or aromatic diacid (e.g., 1,6-hexanedicarboxylic acid, 1,4-cyclohexanedicarboxylic acid, 1,4-terephthalic acid).

The term "alkyl" as used herein refers to a monovalent or bivalent, branched or unbranched saturated hydrocarbon group having from 1 to 20 carbon atoms, typically although, not necessarily, containing 1 to about 12 carbon atoms, such as methyl, ethyl, n-propyl, isopropyl, n-butyl, isobutyl, t-butyl, octyl, and the like. The term alkyl also may include cycloalkyl groups. Thus, for example, the term C6 alkyl would embrace cyclohexyl groups, the term C5 would embrace cyclopentyl groups, the term C4 would embrace cyclobutyl groups, and the term C3 would embrace cyclopropyl groups. In addition, as the alkyl group may be branched or unbranched, any alkyl group of n carbon atoms would embrace a cycloalkyl group of less than n carbons substituted by additional alkyl substituents. Thus, for example, the term C6 alkyl would also embrace methylcyclopentyl groups, or dimethylcyclobutyl or ethylcyclobutyl groups, or trimethylcyclopropyl, ethylmethylcyclopropyl or propylcyclopropyl groups.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like. In like manner as for the term "alkyl", the term "alkenyl" also embraces cycloalkenyl groups, both branched an unbranched with the double bond optionally intracyclic or exocyclic.

Unless otherwise specified, any carbon atom with an open valence may be substituted by an additional functional group. Examples of functional groups include, without limitation: halo, hydroxyl, sulfhydryl, $C_1$-$C_{20}$ alkoxy, $C_2$-$C_{20}$alkenyloxy, $C_2$-$C_{20}$ alkynyloxy, $C_5$-$C_{20}$ aryloxy, acyl (including $C_2$-$C_{20}$ alkylcarbonyl (—CO-alkyl) and $C_6$-$C_{20}$ arylcarbonyl (—CO-aryl)), acyloxy (—O-acyl), $C_2$-$C_{20}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{20}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-substituted $C_1$-$C_{20}$ alkylcarbamoyl (—(CO)—NH($C_1$-$C_{20}$ alkyl)), di-substituted alkylcarbamoyl (—(CO)—N($C_1$-$C_{20}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (C≡N), isocyano (—$N^+$≡$C^-$), cyanato (—O—C≡N), isocyanato (—O—$N^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{20}$ alkyl)-substituted amino, mono- and di-($C_5$-$C_{20}$ aryl)-substituted amino, $C_2$-$C_{20}$ alkylamido (—NH—(CO)-alkyl), $C_5$-$C_{20}$ arylamido (—NH—(CO)-aryl), imino (—CR=NH where R=hydrogen, $C_1$-$C_{20}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{20}$ alkylsulfanyl (—S-alkyl; also termed "alkylthio"), arylsulfanyl (—S-aryl; also termed "arylthiol"), $C_1$-$C_{20}$ alkylsulfinyl (—(SO)-alkyl), $C_5$-$C_{20}$ arylsulfinyl (—(SO)-aryl), $C_1$-$C_{20}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$),-phosphino (—$PH_2$), mono- and di-($C_1$-$C_{20}$ alkyl)-substituted phosphino, mono- and di-($C_5$-$C_{20}$ aryl)-substituted phosphino; and the hydrocarbyl moieties such as $C_1$-$C_{20}$ alkyl (including $C_1$-$C_{18}$ alkyl, further including $C_1$-$C_{12}$ alkyl, and further including $C_1$-$C_6$ alkyl), $C_2$-$C_{20}$ alkenyl (including $C_2$-$C_{18}$ alkenyl, further including $C_2$-$C_{12}$ alkenyl, and further including $C_2$-$C_6$ alkenyl), $C_2$-$C_{20}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{20}$ aryl), and $C_6$-$C_{20}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

In a second aspect, the present disclosure provides a method of making any one of Compound 1 or 1.1 et seq., comprising the step of reducing a humulone, lupulone or isohumulone (e.g., by catalytic hydrogenation) to provide a hydrogenated (e.g., partially or fully hydrogenated humulone, lupulone or isohumulone, and optionally further derivatizing the initial hydrogenation product to form additional Compounds, e.g., esters, ethers, acids, alcohols, aldehydes, ketones, and other derivatives. In some embodiments, the hydrogenation reaction may be preceded by an alkene addition reaction (e.g., hydration or epoxidation and hydrolysis of an exocyclic double bond). In some embodiments, the hydrogenation may be preceded by the acylation or etherification of a hydroxy group. In some embodiments, the hydrogenation may be proceeded by reduction of the exocyclic ketone and optionally further derivatization thereof (e.g., etherification or esterification).

By way of example, and without limiting the scope of the disclosure, any such further derivatization reactions may include one or more of the following (which reactions may be conducted on the original core of the humulone, lupulone, or isohumulone, or on a pendant group itself added via one of the below reactions):

a. oxidizing a primary alcohol to an aldehyde
b. oxidizing a secondary alcohol to ketone
c. reducing a ketone to a secondary alcohol
d. reducing a carboxylic acid to an aldehyde
e. reducing a carboxylic acid to a primary alcohol
f. oxidizing a primary alcohol to an aldehyde
g. addition of a nucleophile to an aldehyde or ketone (e.g., a Grignard reagent or organolithium reagent, or an alkoxide)
h. hydrolyzing a carboxylic ester
i. hydrolyzing a phosphate ester or phosphonate ester
j. hydrolyzing a sulfate or sulfonate ester
k. converting an alcohol to an ether
l. converting a carboxylic acid to an ester
m. hydrating a double bond
n. epoxidizing a double bond followed by ring opening (e.g., with a hydroxide)
o. eliminating a hydroxy group to form a double bond (e.g., via acid-catalyzed elimination or via activation followed by base-catalyzed elimination)
p. deoxygenation (e.g., converting a secondary alcohol to a methylene or a tertiary alcohol to a methine, or a ketone to a methylene).

Exemplary prophetic reactions which might be used to form the various Compounds of the Invention (e.g., Compound 1 et seq.) include the following:

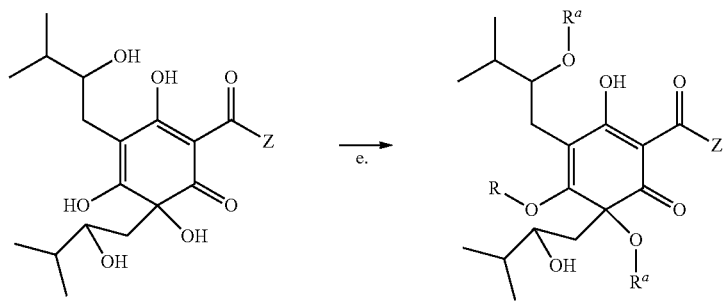

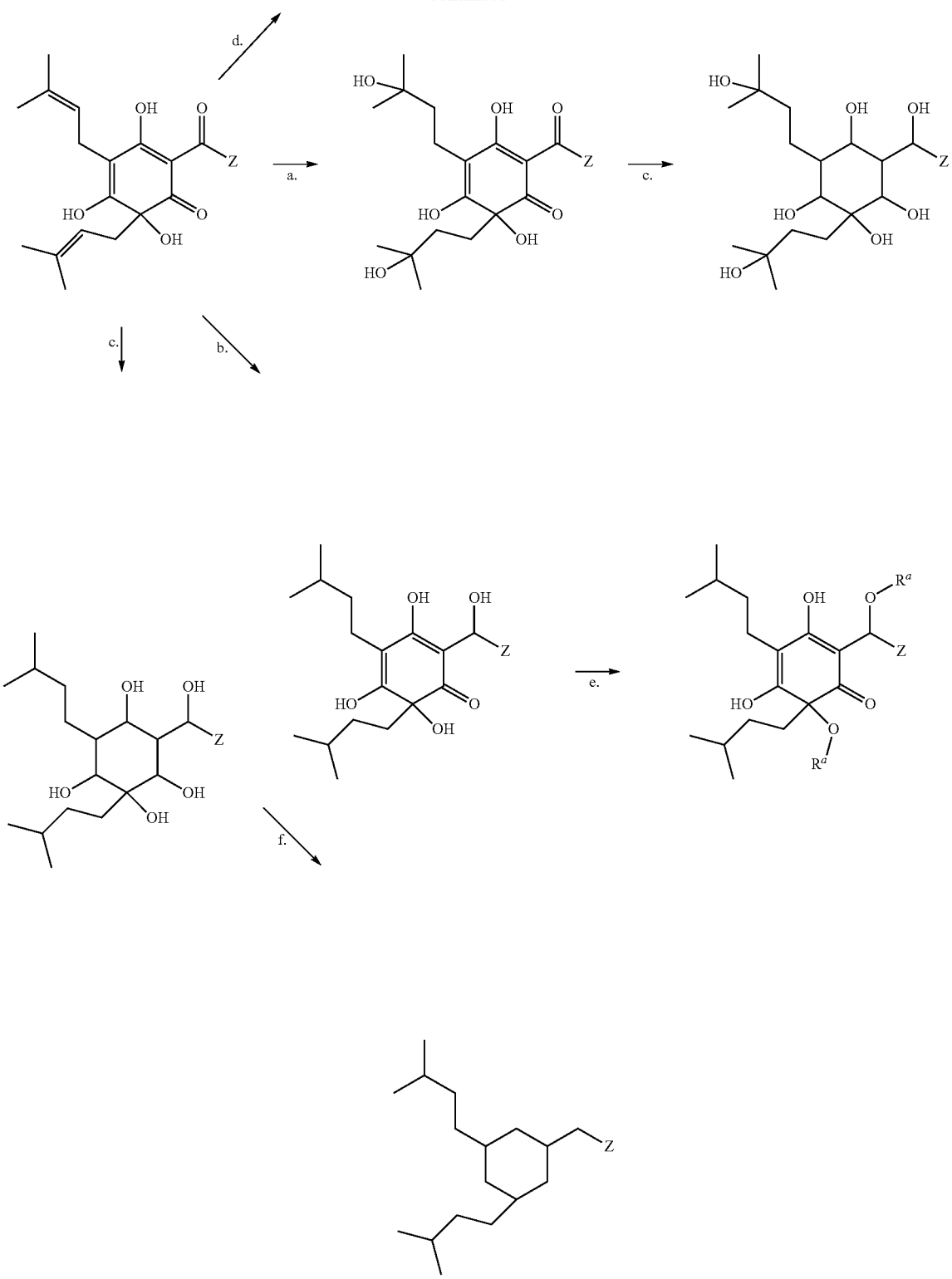
25 26
Z = n-propyl, sec-butyl or isobutyl
a. Hg(OAc)$_2$, H$_2$O, Et$_2$O
b. H$_2$, Pd/C, 1 atm
c. H$_2$, PtO$_2$, 5 atm, 150° C.
d. (1) BH$_3$, THF, (2) H$_2$O$_2$, KOH, H$_2$O
e. R$^a$—Br, K$_2$CO$_3$, ACN (R$^a$ = alkyl) or R$^a$—Cl, Et$_3$N, THF (R$^a$ = —C(O)—alkyl)
f. (1) MeS—C(S)—Cl, pyridine, toluene; (2) Me$_3$B—H$_2$O, toluene Additional exemplary prophetic reaction schemes which might be used to form the various Compounds of the Invention (e.g., Compound 1 et seq.) including the following:

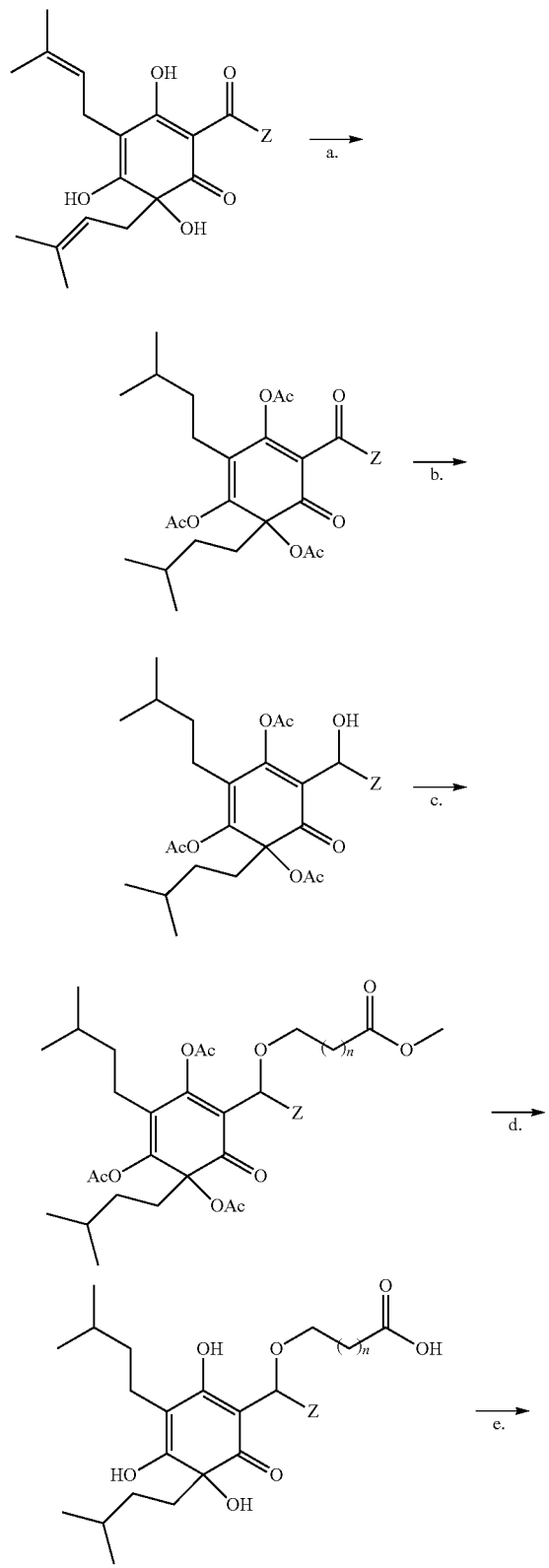

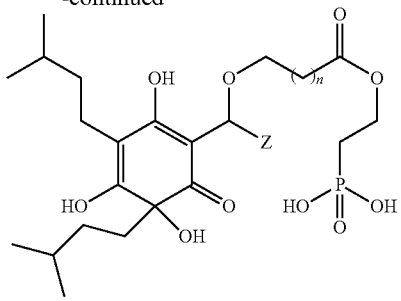

Z = n-propyl, sec-butyl or isobutyl
a. (1) H$_2$, Pd/C, 1 atm; (2) Ac$_2$O, Et$_3$N, DCM
b. NaBH$_4$, THF
c. CH$_3$O—C(O)—(CH$_2$)$_n$CH$_2$Cl, Et$_3$N, THF
d. KOH, H$_2$O, THF
e. (1) Me$_2$PO$_3$CH$_2$CH$_2$OH, DCC, Et$_3$N, DCM; (2) NaOH, H$_2$O, THF While the previous two paragraphs' synthetic schemes present exemplary chemical reactions which may be conducted starting from humulones as shown, it is understood that each of these reactions, or any combination thereof, can be used on any Compound of Formula I, et seq., described herein, including, but not limited to, humulone, cohumulone, adhumulone, lupulone, colupulone, adlupulone, cis-isohumulone, trans-isohumulone, or any ether, ester, or other derivative thereof. The use of the humulone nucleus in the above schemes is merely by way of example.

Suitable solvents and reactions conditions (concentration, time, temperature) for the conducting the above reactions are generally known to those skilled in the art and are not limited in any way in the present disclosure. Depending on the choice of reagents, suitable solvents may include one or more of apolar, polar protic and/or polar aprotic solvents, for example hydrocarbons, ethers, and esters.

In some embodiments, one or more of the above reactions may be carried out at a temperature of –100° C. to 300° C. For example, depending on the reaction, suitable temperature ranges may include –100 to –50° C., –50 to –25° C., –25 to –0° C., 0 to 25° C., 20 to 30° C., 30 to 60° C., 60 to 100° C., 100 to 150° C., 150 to 200° C., or 200 to 300° C. In some embodiments, one or more of the above reactions may be carried out for 0.1 to 100 hours. For example, depending on the reaction, suitable reaction times may include 0.1 to 0.25 hours, 0.25 to 0.5 hours, 0.5 to 1.0 hours, 1-2 hours, 2-6 hours, 6-12 hours, 12-24 hours, 24-48 hours, or 48-96 hours.

Where hydrogenation is employed, suitable hydrogen pressures range from 1 atmosphere to 20 atmospheres, e.g., 1 to 3 atmospheres, 3 to 6 atmospheres, 6 to 10 atmospheres, or 10 to 20 atmospheres. Hydrogenation reactions, depending on the substrate and the type of bond being reduced, may be conducted with any of the catalysts known in the art, including homogenous and heterogenous catalysts. Suitable catalysts may include palladium, platinum, iridium, ruthenium, and rhodium catalysts. In some embodiments, transfer hydrogenation (e.g., using ammonium formate as the hydrogen donor) may be used instead of hydrogen gas.

Oxidation and reduction reactions may be carried out according to standard methods in the art. Suitable oxidation reagents generally include chromium compounds (e.g., chromium trioxide, chromic acid, pyridinium chlorochromate, alkali metal chromates, alkali metal dichromates), permanganate compounds (e.g., potassium permanganate), perborate compounds (e.g., sodium perborate), osmium compounds (e.g., osmium tetroxide), peroxide compounds (e.g., hydrogen peroxide, peracetic acid, trifluoroperacetic acid, meta-chloroperoxybenzoic acid), nitric acid, chlorine compounds (e.g., chlorine dioxide, hypochlorous acid or salts, perchloric acid or salts), hypervalent iodine compounds (e.g., 2-iodosobenzoic acid, Dess-Martin periodinane), and oxygen species (e.g., oxygen or ozone). Suitable reducing agents generally include metal hydride agents (e.g., sodium borohydride, sodium triacetoxyborohydride, lithium borohydride, lithium tri-sec-butyl borohydride, sodium cyanoborohydride, lithium aluminum hydride, diisobutylaluminum hydride, sodium bis(methoxyethoxy) aluminum hydride, zinc amalgam, zinc in acid (e.g., acetic acid or hydrochloric acid), formic acid, iron(II) salts, tin(II) salts, and boranes (e.g., borane-THF complex, borane-dimethylsulfide complex, 9-borabicyclononane).

Suitable hydrolysis conditions are known in the art and generally include acidic conditions (e.g., hydrochloric acid, sulfuric acid, phosphoric acid, acetic acid), or basic conditions (e.g., salts of hydroxide, carbonate, bicarbonate, alkoxides) in suitable solvent, often mixture of water with an organic solvent (e.g., methanol, ethanol, t-butanol, THF, acetonitrile).

Suitable alkylation and acylation conditions are known in the art, and generally include reacting a hydroxy compound with an alkyl halide or acyl halide in the presence of a base (e.g., an organic base, such as triethylamine, diisopropylamine, N-methylmorpholine, pyridine or dimethylaminopyridine, or an inorganic base, such as an alkali metal hydroxide, carbonate, or bicarbonate) in a suitable solvent. Other acylation conditions include those assisted by an activating agent, such as for less reactive alcohols. Suitable activating agents include diimides (e.g., dicyclohexylcarbodiimide, diisopropylcarbodiimide, 1-ethyl-3-(3-dimethylaminopropyl)carbodiimide), 1,1-carbonyldiimidazole, thionyl chloride, and oxalyl chloride.

Compounds according to the present disclosure may be used for numerous purposes, including, but not limited to, as emollients, solubilizers, anti-frizz agents, lubricants, carriers, conditioners, surfactants, adjuvants, dispersants, emulsifiers, fuels, paraffins, candles, and as a precursor for polymers, film-formers, resins and compositions. Thus, in another aspect, the present disclosure provides for the use of Compound 1 or any of 1.1 et seq., for any of these purposes.

In another aspect, the present disclosure provides a composition comprising Compound 1 or any of 1.1 et seq., optionally in admixture with one or more pharmaceutically acceptable, cosmetically acceptable, or industrially acceptable excipients or carriers, for example, solvents, oils, surfactants, emollients, diluents, glidants, abrasives, humectants, polymers, plasticizer, catalyst, antioxidant, coloring agent, flavoring agent, fragrance agent, antiperspirant agent, antibacterial agent, antifungal agent, hydrocarbon, stabilizer, or viscosity controlling agent. In some embodiments, the composition is a pharmaceutical composition, or a cosmetic composition, or a sunscreen composition, or a plastic composition, or a lubricant composition, or a personal care composition (e.g., a soap, skin cream or lotion, balm, shampoo, body wash, hydrating cream, deodorant, antiperspirant, after-shave lotion, cologne, perfume, or other hair care or skin care product), or a cleaning composition (e.g., a surface cleaner, a metal cleaner, a wood cleaner, a glass cleaner, a body cleaner such as a soap, a dish-washing detergent, or a laundry detergent), or an air freshener.

The compounds of the present disclosure, e.g., Compound 1, et seq., may be used with, for example: perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, antiperspirants, shampoo, cologne, shower gel, hair spray, pet litter, lubricating oils, heating oils, and diesel fuels.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

In some embodiments, the present disclosure provides personal care compositions including, but not limited to, soaps (liquid or solid), body washes, skin and hair cleansers, skin creams and lotions (e.g., facial creams and lotions, face oils, eye cream, other anti-wrinkle products), ointments, sunscreens, moisturizers, hair shampoos and/or conditioners, deodorants, antiperspirants, other conditioning products for the hair, skin, and nails (e.g., shampoos, conditioners, hair sprays, hair styling gel, hair mousse), decorative cosmetics (e.g., nail polish, eye liner, mascara, lipstick, foundation, concealer, blush, bronzer, eye shadow, lip liner, lip balm,) and dermocosmetics.

In some embodiments, the personal care compositions may include organically-sourced ingredients, vegan ingredients, gluten-free ingredients, environmentally-friendly ingredients, natural ingredients (e.g. soy oil, beeswax, rosemary oil, vitamin E, coconut oil, herbal oils etc.), comedogenic ingredients, natural occlusive plant based ingredients (e.g. cocoa, shea, mango butter), non-comedogenic ingredients, bakuchiol (a plant derived compound used as a less-irritating, natural alternative to retinol), color active ingredients (e.g., pigments and dyes); therapeutically-active ingredients (e.g., vitamins, alpha hydroxy acids, corticosteroids, amino acids, collagen, retinoids, antimicrobial compounds), sunscreen ingredients and/or UV absorbing compounds, reflective compounds, oils (such as castor oil and olive oil, or high-viscosity oils), film formers, high molecular weight esters, antiperspirant active ingredients, glycol solutions, water, alcohols, emulsifiers, gellants, emollients, water, polymers, hydrocarbons, conditioning agents, and/or aliphatic esters.

In some embodiments, the present compositions are gluten free.

In some embodiments, the present compositions are formulated as oil-in-water emulsions, or as water-in-oil emulsions. In some embodiments, the compositions may further comprise one or more hydrocarbons, such as heptane, octane, nonane, decane, undecane, dodecane, isododecane, tridecane, tetradecane, pentadecane, hexadecane, heptadecane, octadecane, nonadecane, henicosane, docosane, and tricosane, and any saturated linear or saturated branched isomer thereof.

In some embodiments, the present disclosure provides a fuel composition which comprises, or consists of, fully reduced (e.g., saturated and optionally oxygenated) compounds of the present disclosure, for use as a fuel or fuel component, e.g., as diesel fuel. For example, the compounds according to embodiments 1.28 and 1.30, supra, are C21 or C25 hydrocarbons having from zero to five oxygen atoms, and these are particularly suitable for use as fuels or as fuel components (e.g., as diesel fuels, which typically comprise C9-C25 hydrocarbons). Thus, the compounds may be formulated into a fuel composition optionally blended with other typical petroleum-derived hydrocarbons, such as aliphatic C9-C25 hydrocarbons. There has been an increasing need for oxygenated fuels to improve combustion performance in engines, and the oxygenated saturated hydrocarbons of the present disclosure may be particularly suited to such purposes.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore, as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

In the present specification, the structural formula of the compounds may represent a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formulas describe herein. It is noted that any crystal form, crystal form mixture, or anhydride or hydrate thereof is included in the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

Any compound disclosed herein which comprises an acidic or basic group, such as a carboxylic acid group or amine group, may be formed or used in its free acid form or in its free base form, or as a salt. As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as Na+, K+, Li+, alkali earth metal salts such as Mg2+ or Ca2+, or organic amine salts, or organic phosphonium salts.

All percentages used herein, unless otherwise indicated, are by volume.

All ratios used herein, unless otherwise indicated, are by molarity.

The compounds disclosed herein can be prepared through a number of straightforward chemical procedures, as described above, which are generally known to the skilled artisan. For example, as provided in *March's Advanced Organic Chemistry: Reactions, Mechanisms, and Structure* by Michael B. Smith and Jerry March (6$^{th}$ Ed., John Wiley & Sons 2007). Compounds according to the present disclosure may be isolated and purified according to procedures known in the art, for example, extraction. fractional distillation, crystallization and chromatography.

Methods for extracting the raw *Humulus* compounds from plant parts are known in the art. See, for example, Stevens, R., Chem. Rev. 67(1):19-71 (1967), and Bren et al., *Nutrients*, 11:257 (2019). For example, for the isolation of humulones and lupulones, supercritical carbon dioxide ($sCO_2$) extraction is a popular method. Typical extraction conditions are 40-50° C. and 150-400 bar pressure. Optionally, small amounts of alcoholic solvents, such as ethanol, can be added. Typically dried, ground hops are used as the starting material for the extraction. Optionally, the oil can be chilled to about −20° C. to precipitate out undesired waxes. Further optionally, the resulting oil can then be heated to about 100 to 120° C. to cause thermal decarboxylation of the cannabinoid acids present. The various organic molecules can be separated by traditional methods, such as distillation (e.g., vacuum distillation), crystallization (e.g., from heptane), or chromatography, to provide various mixtures of components for further chemical elaboration according to the procedures described herein.

I claim:

1. A composition comprising a compound which is a hydrogenated derivative of a humulone, lupulone or isohumulone, comprising the compound in admixture with one or more pharmaceutically acceptable, cosmetically acceptable, or industrially acceptable excipients or carriers selected from solvents, oils, surfactants, emollients, diluents, glidants, abrasives, humectants, polymers, plasticizers, catalysts, antioxidants, coloring agents, flavoring agents, fragrance agents, antiperspirant agents, antibacterial agents, antifungal agents, hydrocarbons, stabilizers, and viscosity controlling agents.

2. The composition of claim 1, wherein the compound is a hydrogenated derivative of humulone, cohumulone, or adhumulone.

3. The composition of claim 1, wherein the compound is a hydrogenated derivative of lupulone, colupulone, or adlupulone.

4. A compound which has a structure selected from the following:

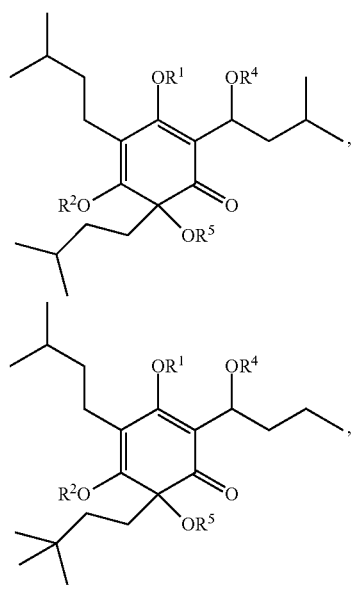

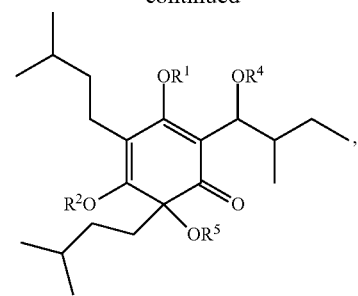
,
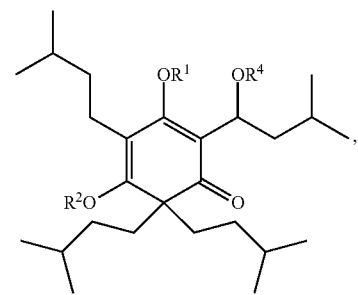
,
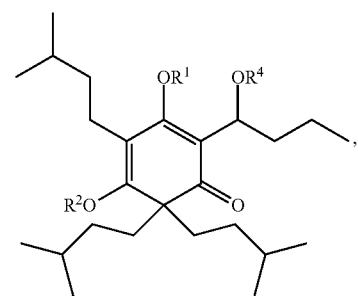
,
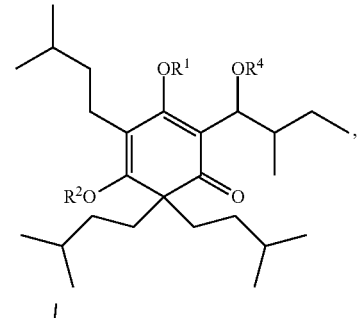
,
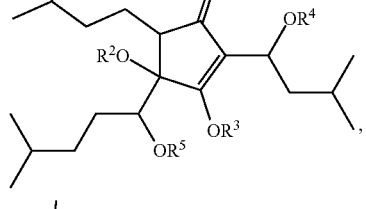
,
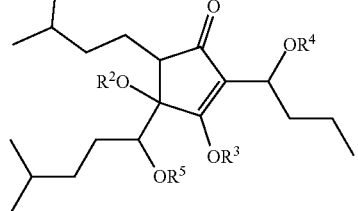
,
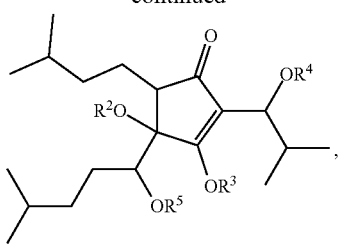
,
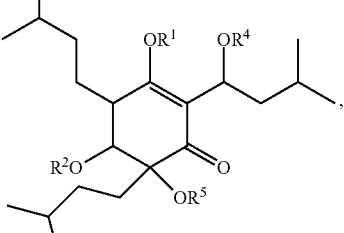
,
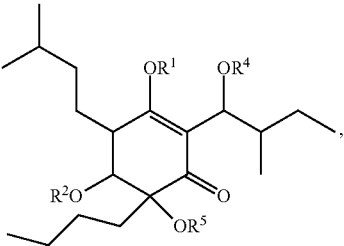
,
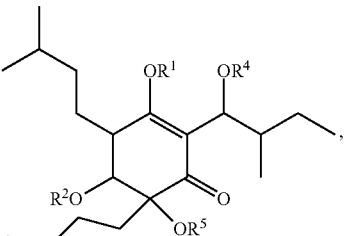
,
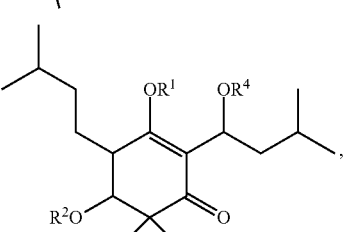
,
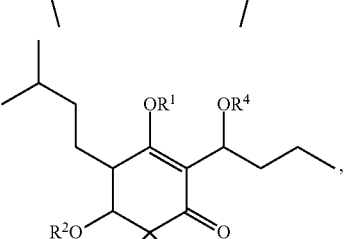
, 35
-continued
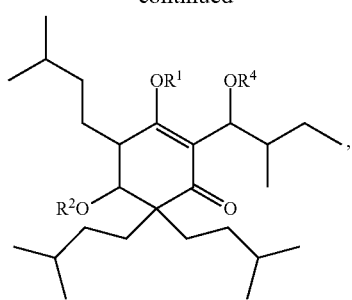
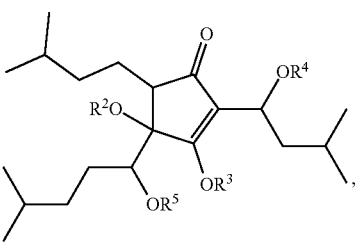
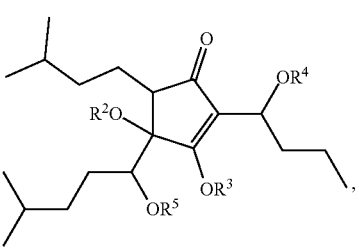
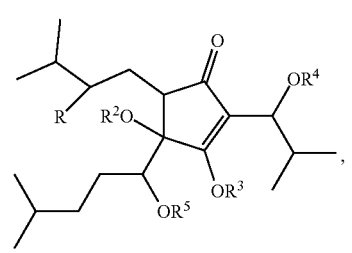
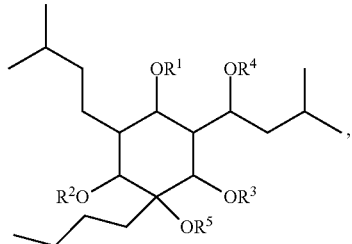
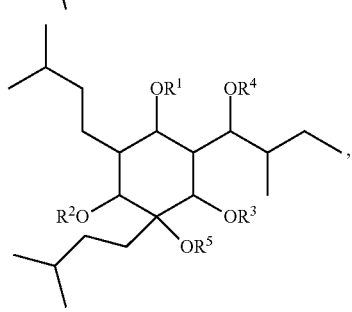
36
-continued
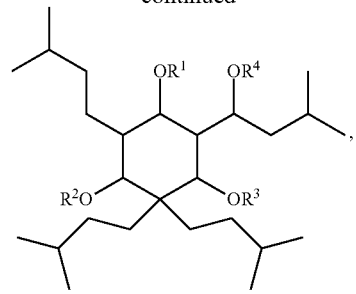
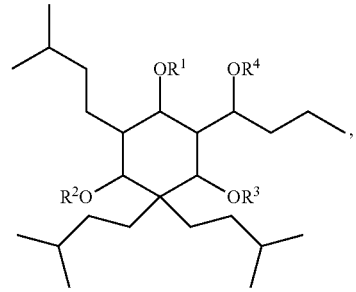
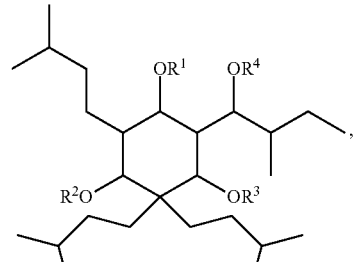
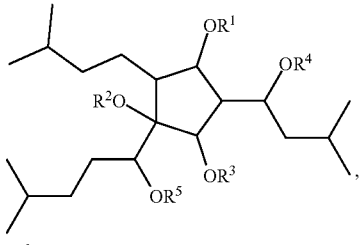
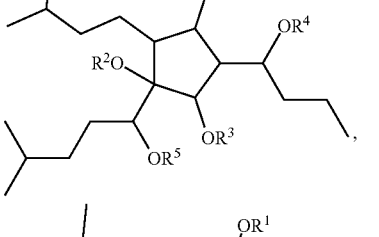, and
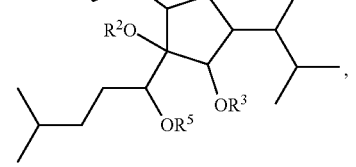
wherein:
$R^1$, $R^2$, $R^3$, $R^4$, and $R^5$, are each independently selected from H, $C_{1-21}$alkyl, —C(O)—$C_{1-21}$alkyl, $C_{2-21}$alkenyl, —C(O)—$C_{2-21}$alkenyl, $C_{3-7}$cycloalkyl, —C(O)—$C_{3-7}$cycloalkyl, $C_{1-6}$haloalkyl, —C(O)—$C_{1-6}$haloalkyl, (CH₂CH₂O)nCH₂CH₂OH, (CH₂CH(CH₃)O)nCH₂CH(CH₃)OH, C₁₋₂₁alkyl-OH, —C(O)—C₁₋₂₁alkyl-OH, C₁₋₂₁alkyl-C(O)—OC₁₋₆alkyl, C(O)—C₁₋₂₁alkyl-C(O)—OC₁₋₆alkyl, C₁₋₂₁alkyl-COOH, —C(O)—C₁₋₂₁alkyl-COOH, —P(O)(OC₁₋₂₁alkyl)(OC₁₋₂₁alkyl), —SO₂OC₁₋₂₁alkyl, —SO₂C₁₋₂₁alkyl, C₁₋₂₁alkyl-P(O)(OC₁₋₆alkyl)(OC₁₋₆alkyl), —C(O)—C₁₋₂₁alkyl-P(O)(OC₁₋₆alkyl)(OC₁₋₆alkyl), C₁₋₂₁alkyl-P(O)(OH)(OC₁₋₆alkyl), —C(O)—C₁₋₂₁alkyl-P(O)(OH)(OC₁₋₆alkyl), C₁₋₂₁alkyl-P(O)(OH)₂, —C(O)—C₁₋₂₁alkyl-P(O)(OH)₂, C₁₋₂₁alkyl-SO₂OC₁₋₆alkyl), —C(O)—C₁₋₂₁alkyl-SO₂₀C₁₋₆alkyl, C₁₋₂₁alkyl-SO₃H, and —C(O)—C₁₋₂₁alkyl-SO₃H; or any of R¹, R², R³, or R⁴, is absent; and wherein each n is independently an integer selected from 0 to 20.

5. The composition according to claim 1, wherein the compound has a structure selected from:

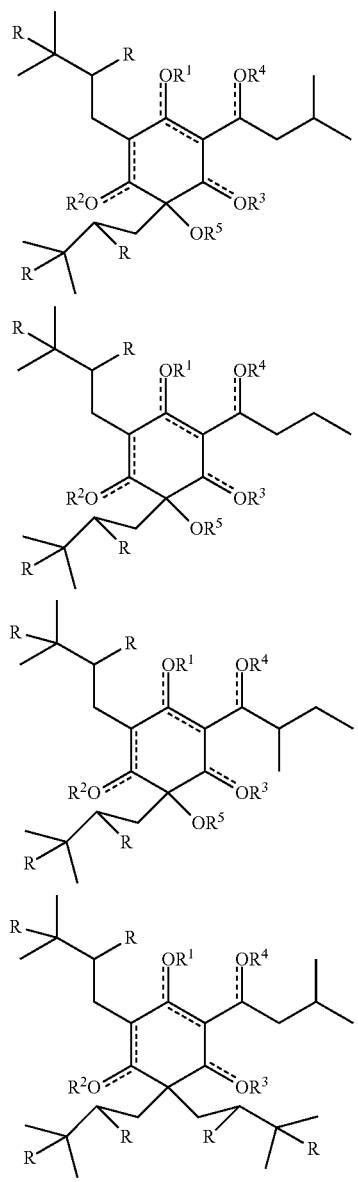

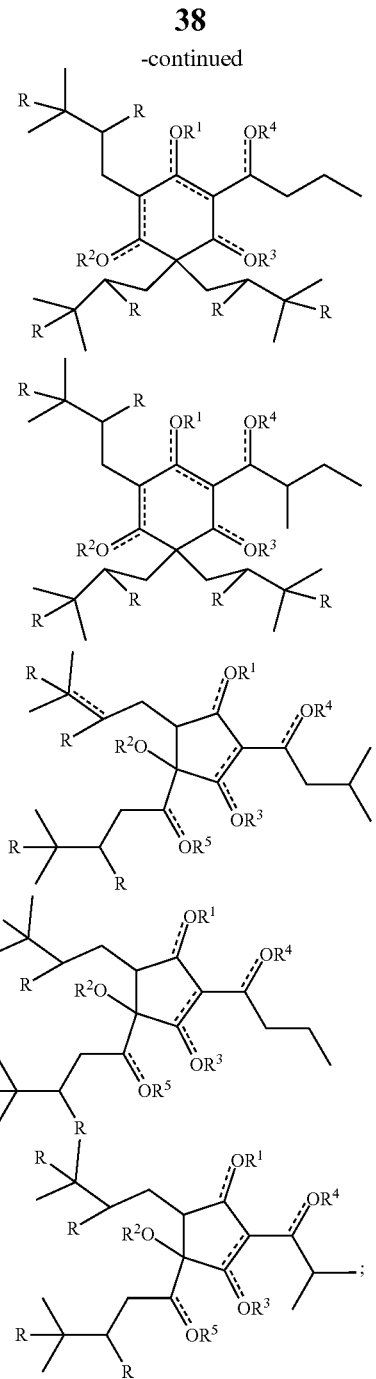

wherein each R is independently H or OH, R¹, R², R³, R⁴, and R⁵, are each independently selected from H, C₁₋₂₁alkyl, —C(O)—C₁₋₂₁alkyl, C₂₋₂₁alkenyl, —C(O)—C₂₋₂₁alkenyl, C₃₋₇cycloalkyl,—C(O)—C₃₋₇cycloalkyl, C₁₋₆haloalkyl,-C(O)—C₁₋₆haloalkyl, (CH₂CH₂O)nCH₂CH₂OH, (CH₂CH(CH₃)O)nCH₂CH(CH₃)OH, C₁₋₂₁alkyl-OH, —C(O)—C₁₋₂₁alkyl-OH, C₁₋₂₁alkyl—C(O)—OC₁₋₆alkyl, C(O)—C₁₋₂₁alkyl—C(O)—OC₁₋₆alkyl, C₁₋₂₁alkyl-COOH, —C(O)—C₁₋₂₁alkyl-COOH, —P(O)(OC₁₋₂₁alkyl)(OC₁₋₂₁alkyl), —SO₂₀C₁₋₂₁alkyl,-SO₂C₁₋₂₁alkyl, C₁₋₂₁alkyl —P(O)(OC₁₋₆alkyl)(OC₁₋₆alkyl),-C(O)-C₁₋₂₁alkyl-P(O)(OC₁₋₆alkyl)(OC₁₋₆alkyl), C₁₋₂₁alkyl —P(O)(OH)(OC₁₋₆alkyl),-C(O)-C₁₋₂₁alkyl-P(O)(OH)(OC₁₋₆alkyl), C₁₋₂₁alkyl-P(O)(OH)₂, —C(O)—C₁₋₂₁alkyl-P(O)

(OH)$_2$, C$_{1-21}$alkyl—SO$_2$$_0$C$_{1-6}$alkyl), —C(O)—C$_{1-21}$alkyl-SO$_2$OC$_{1-6}$alkyl, C$_{1-21}$alkyl—SO$_3$H, and —C(O)—C$_{1-21}$alkyl-SO$_3$H; or any of R$^1$, R$^2$, R$^3$, or R$^4$, is absent; and wherein each n is independently an integer selected from 0 to 20;

wherein each ═══ is either a single bond or a double bond, and wherein each ─── is either a single bond or is absent; and provided that the bonds ═══ and ─── are selected such that all carbon atoms and oxygen atoms to which these bonds are attached have a total of four attached bonds inclusive of single and double bonds.

6. The composition according to claim 1, wherein the compound has a structure selected from:

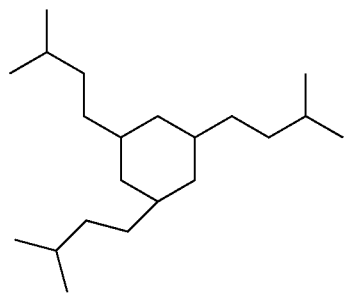

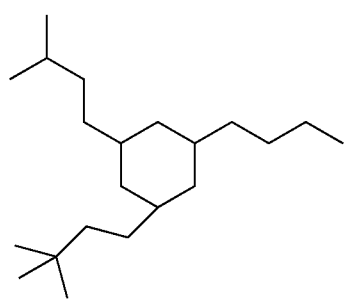

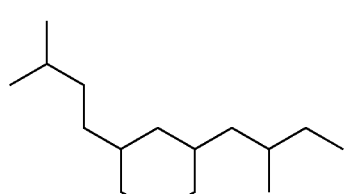

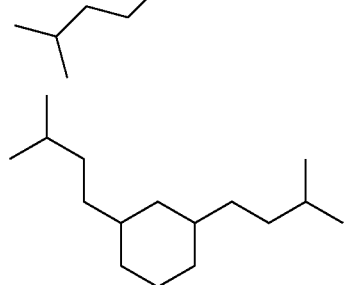

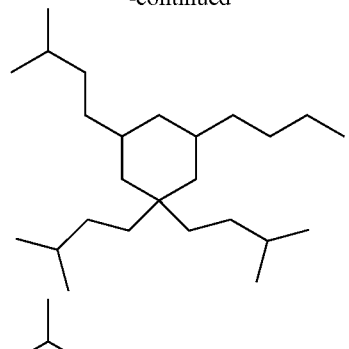

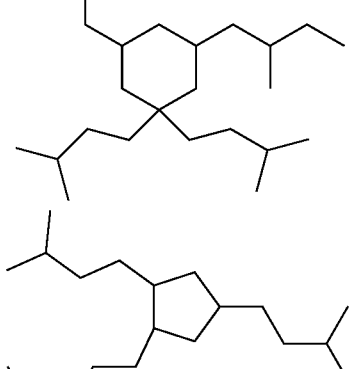

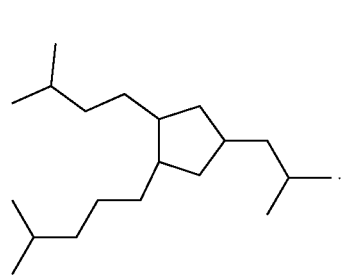

and wherein R$^1$, R$^2$, R$^3$, R$^4$, and R$^5$, are each independently selected from H, C$_{1-21}$alkyl, —C(O)—C$_{1-21}$alkyl, C$_{2-21}$alkenyl, —C(O)—C$_{2-21}$alkenyl, C$_{3-7}$cycloalkyl, —C(O)—C$_{3-7}$cycloalkyl, C$_{1-6}$haloalkyl, —C(O)—C$_{1-6}$haloalkyl, (CH$_2$CH$_2$O)nCH$_2$CH$_2$OH, (CH$_2$CH(CH$_3$)O)nCH$_2$CH(CH$_3$)OH, C$_{1-21}$alkyl-OH, —C(O)—C$_{1-21}$alkyl-OH, C$_{1-21}$alkyl-C(O)—OC$_{1-6}$alkyl, C(O)—C$_{1-21}$alkyl-C(O)—OC$_{1-6}$alkyl, C$_{1-21}$alkyl-COOH, —C(O)—C$_{1-21}$alkyl-COOH, —P(O)(OC$_{1-21}$alkyl)(OC$_{1-21}$alkyl), —SO$_2$OC$_{1-21}$alkyl, —SO$_2$C$_{1-21}$alkyl, C$_{1-21}$alkyl-P(O)(OC$_{1-6}$alkyl)(OC$_{1-6}$alkyl), —C(O)—C$_{1-21}$alkyl-P(O)(OC$_{1-6}$alkyl)(OC$_{1-6}$alkyl), C$_{1-21}$alkyl-P(O)(OH)(OC$_{1-6}$alkyl), —C(O)—C$_{1-21}$alkyl-P(O)(OH)(OC$_{1-6}$alkyl), C$_{1-21}$alkyl-P(O)(OH)$_2$, —C(O)—C$_{1-21}$alkyl-P(O)(OH)$_2$, C$_{1-21}$alkyl-SO$_2$OC$_{1-6}$alkyl), —C(O)—C$_{1-21}$alkyl-SO$_2$OC$_{1-6}$alkyl, C$_{1-21}$alkyl-SO$_3$H, and —C(O)—C$_{1-21}$alkyl-SO$_3$H; or any of R$^1$, R$^2$, R$^3$, or R$^4$, is absent; and wherein each n is independently an integer selected from 0 to 20.

wherein each === is either a single bond or a double bond, and wherein each === is either a single bond or is absent; and provided that the bonds === and === are selected such that all carbon atoms and oxygen atoms to which these bonds are attached have a total of four attached bonds inclusive of single and double bonds.

7. The compound of claim 4, wherein the compound has a structure selected from:

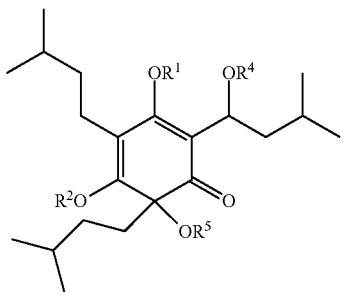

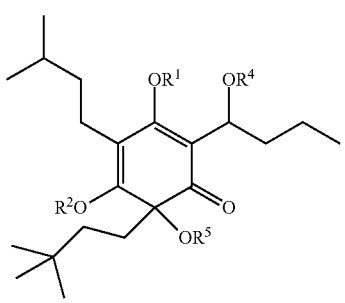

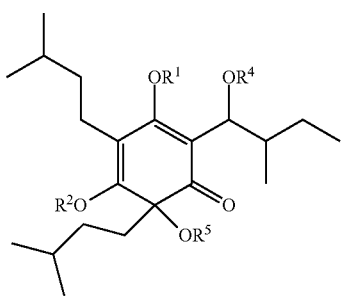

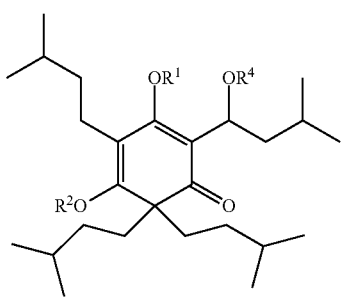

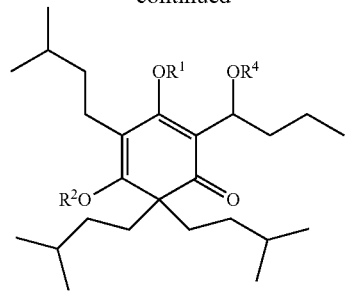

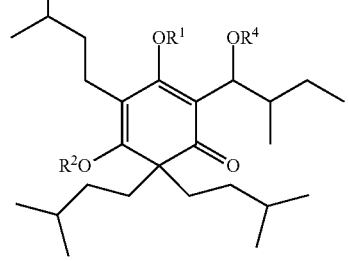

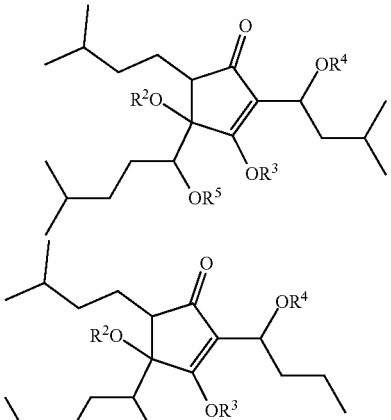

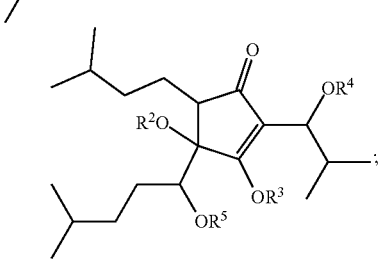

and wherein R$^1$, R$^2$, R$^3$, R$^4$, and R$^5$ are each independently selected from H, C$_{1-21}$alkyl, —C(O)—C$_{1-21}$alkyl, C$_{2-21}$alkenyl, —C(O)-C$_{2-21}$alkenyl, C$_{3-7}$cycloalkyl, —C(O)—C$_{3-7}$cycloalkyl, C$_{1-6}$haloalkyl, —C(O)—C$_{1-6}$haloalkyl, (CH$_2$CH$_2$O)nCH$_2$CH$_2$OH, (CH$_2$CH(CH$_3$)O)nCH$_2$CH(CH$_3$)OH, C$_{1-21}$alkyl-OH, —C(O)—C$_{1-21}$alkyl-OH, C$_{1-21}$alkyl-C(O)—OC$_{1-6}$alkyl, C(O)—C$_{1-21}$alkyl-C(O)—OC$_{1-6}$alkyl, C$_{1-21}$alkyl-COOH, —C(O)—C$_{1-21}$alkyl-COOH, —P(O)(OC$_{1-21}$alkyl)(OC$_{1-21}$alkyl), —SO$_2$OC$_{1-21}$alkyl, —SO$_2$C$_{1-21}$alkyl, C$_{1-21}$alkyl-P(O)(OC$_{1-6}$alkyl)(OC$_{1-6}$alkyl), —C(O)—C$_{1-21}$alkyl-P(O)(OC$_{1-6}$alkyl)(OC$_{1-6}$alkyl), C$_{1-21}$alkyl-P(O)(OH)(OC$_{1-6}$alkyl), —C(O)—C$_{1-21}$alkyl-P(O)(OH)(OC$_{1-6}$alkyl), C$_{1-21}$alkyl-P(O)(OH)$_2$, —C(O)—C$_{1-21}$alkyl-P(O)(OH)$_2$, C$_{1-21}$alkyl-SO$_2$OC$_{1-6}$alkyl), —C(O)—C$_{1-21}$alkyl-SO$_2$OC$_{1-6}$alkyl, C$_{1-21}$alkyl- SO₃H, and —C(O)—C₁₋₂₁alkyl-SO₃H; or any of $R^1$, $R^2$, $R^3$, or $R^4$ is absent; and wherein each n is independently an integer selected from 0 to 20.

8. The compound of claim 4, wherein the compound has a structure selected from:

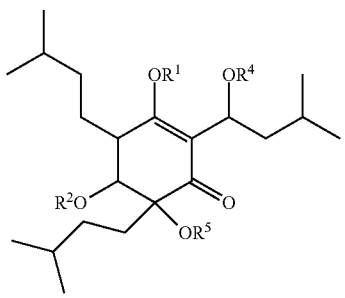

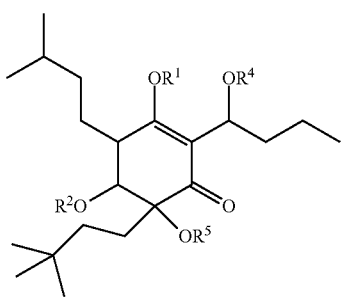

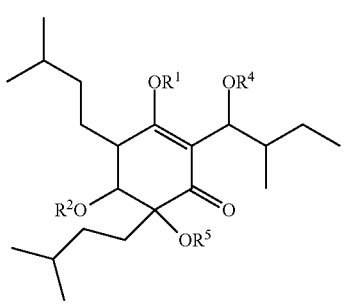

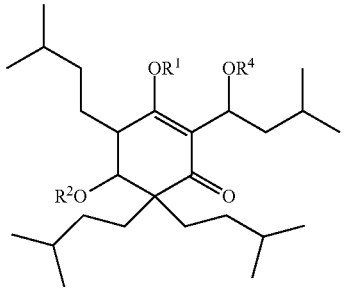

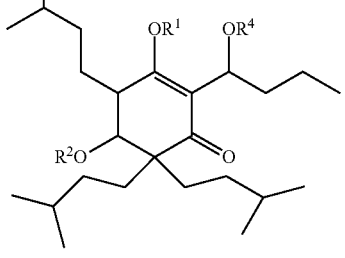

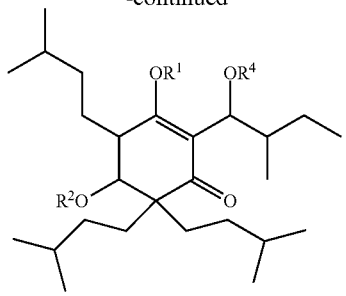

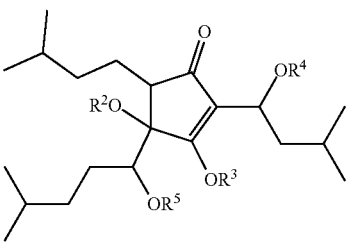

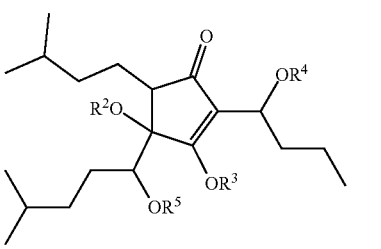

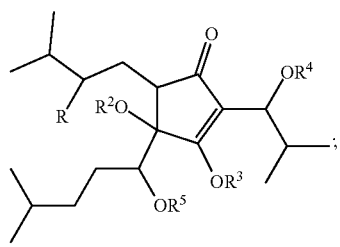

and

;

wherein $R^1$, $R^2$, $R^3$, $R^4$, and $R^5$ are each independently selected from H, C₁₋₂₁alkyl, —C(O)—C₁₋₂₁alkyl, C₂₋₂₁alkenyl, —C(O)—C₂₋₂₁alkenyl, C₃₋₇cycloalkyl, —C(O)—C₃₋₇cycloalkyl, C₁₋₆haloalkyl, —C(O)—C₁₋₆haloalkyl, (CH₂CH₂O)nCH₂CH₂OH, (CH₂CH(CH₃)O)nCH₂CH(CH₃)OH, C₁₋₂₁alkyl-OH, —C(O)—C₁₋₂₁alkyl-OH, C₁₋₂₁alkyl-C(O)—OC₁₋₆alkyl, C(O)—C₁₋₂₁alkyl-C(O)—OC₁₋₆alkyl, C₁₋₂₁alkyl-COOH, —C(O)—C₁₋₂₁alkyl-COOH, —P(O)(OC₁₋₂₁alkyl)(OC₁₋₂₁alkyl), —SO₂OC₁₋₂₁alkyl, —SO₂C₁₋₂₁alkyl, C₁₋₂₁alkyl-P(O)(OC₁₋₆alkyl)(OC₁₋₆alkyl), —C(O)—C₁₋₂₁alkyl-P(O)(OC₁₋₆alkyl)(OC₁₋₆alkyl), C₁₋₂₁alkyl-P(O)(OH)(OC₁₋₆alkyl), —C(O)—C₁₋₂₁alkyl-P(O)(OH)(OC₁₋₆alkyl), C₁₋₂₁alkyl-P(O)(OH)₂, —C(O)—C₁₋₂₁alkyl-P(O)(OH)₂, C₁₋₂₁alkyl-SO₂OC₁₋₆alkyl), —C(O)—C₁₋₂₁alkyl-SO₂OC₁₋₆alkyl, C₁₋₂₁alkyl-SO₃H, and —C(O)—C₁₋₂₁alkyl-SO₃H; or any of $R^1$, $R^2$, $R^3$, or $R^4$ is absent; and wherein each n is independently an integer selected from 0 to 20.

9. The compound of claim 4, wherein the compound has a structure selected from:

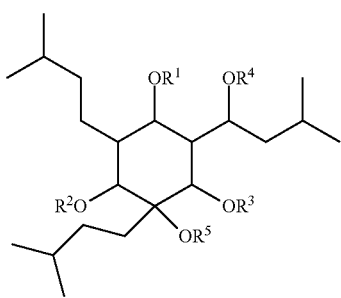

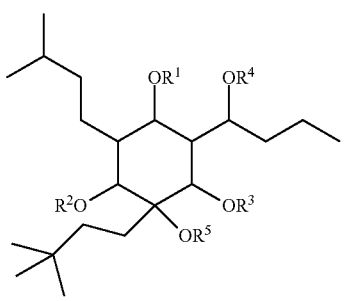

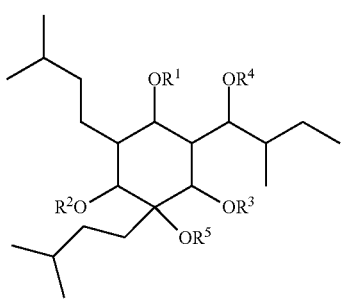

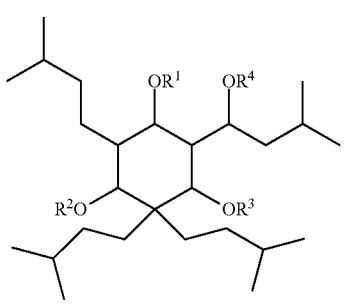

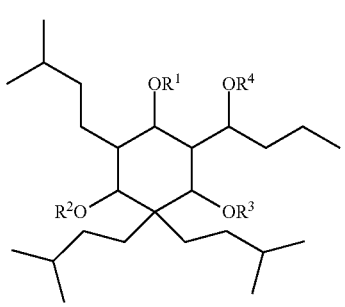

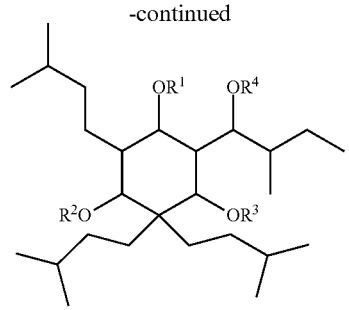

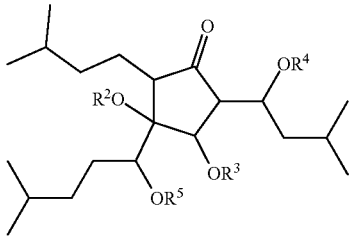

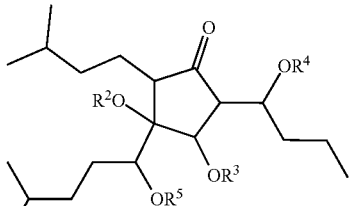

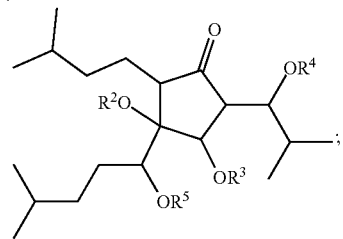

wherein $R^1$, $R^2$, $R^3$, $R^4$, and $R^5$ are each independently selected from H, $C_{1-21}$alkyl, —C(O)—$C_{1-21}$alkyl, $C_{2-21}$alkenyl, —C(O)-$C_{2-21}$alkenyl, $C_{3-7}$cycloalkyl, —C(O)—$C_{3-7}$cycloalkyl, $C_{1-6}$haloalkyl, —C(O)—$C_{1-6}$haloalkyl, $(CH_2CH_2O)nCH_2CH_2OH$, $(CH_2CH(CH_3)O)nCH_2CH(CH_3)OH$, $C_{1-21}$alkyl-OH, —C(O)—$C_{1-21}$alkyl-OH, $C_{1-21}$alkyl-C(O)—$OC_{1-6}$alkyl, C(O)—$C_{1-21}$alkyl-C(O)—$OC_{1-6}$alkyl, $C_{1-21}$alkyl-COOH, —C(O)—$C_{1-21}$alkyl-COOH, —P(O)($OC_{1-21}$alkyl)($OC_{1-21}$alkyl), —$SO_2OC_{1-21}$alkyl, —$SO_2C_{1-21}$alkyl, $C_{1-21}$alkyl-P(O)($OC_{1-6}$alkyl)($OC_{1-6}$alkyl), —C(O)—$C_{1-21}$alkyl-P(O)($OC_{1-6}$alkyl)($OC_{1-6}$alkyl), $C_{1-21}$alkyl-P(O)(OH)($OC_{1-6}$alkyl), —C(O)—$C_{1-21}$alkyl-P(O)(OH)($OC_{1-6}$alkyl), $C_{1-21}$alkyl-P(O)(OH)$_2$, —C(O)—$C_{1-21}$alkyl-P(O)(OH)$_2$, $C_{1-21}$alkyl-$SO_2OC_{1-6}$alkyl), —C(O)—$C_{1-21}$alkyl-$SO_2OC_{1-6}$alkyl, $C_{1-21}$alkyl-$SO_3H$, and —C(O)—$C_{1-21}$alkyl-$SO_3H$; or any of $R^1$, $R^2$, $R^3$, or $R^4$ is absent; and wherein each n is independently an integer selected from 0 to 20.

10. The compound according to claim 4, wherein each group R is H; and wherein:
 a. $R^1$, $R^2$, and $R^5$ are each H, and $R^3$ and $R^4$ are absent, or
 b. $R^2$ and $R^3$ are each H, and $R^1$, $R^4$, and $R^5$ are absent, or
 c. $R^1$, $R^2$, $R^5$ and $R^3$ are each H; or
 d. $R^1$, $R^2$, $R^3$, $R^4$, and $R^5$ are each H.

11. The compound of claim 4, wherein the compound has a structure selected from:
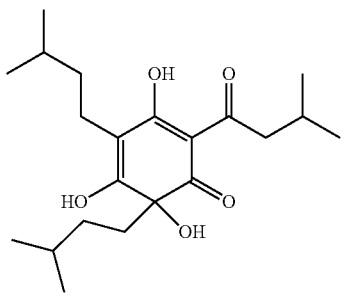
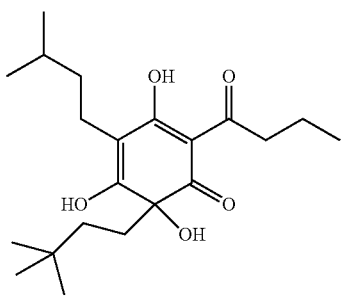
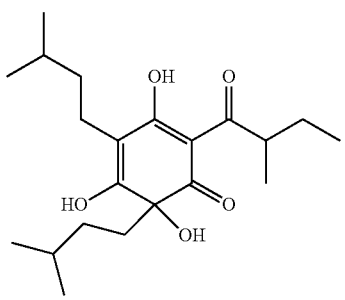
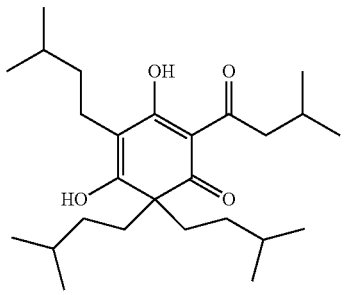
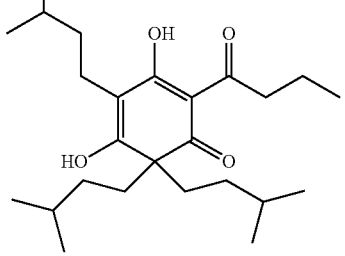
-continued
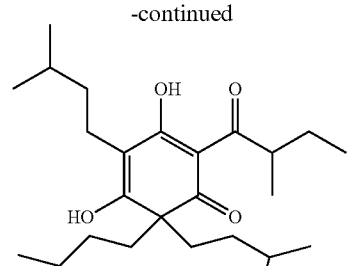
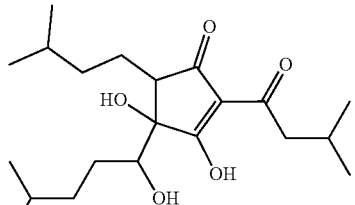
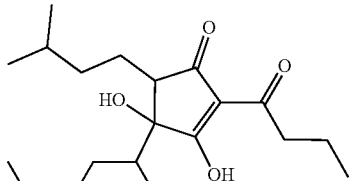
and
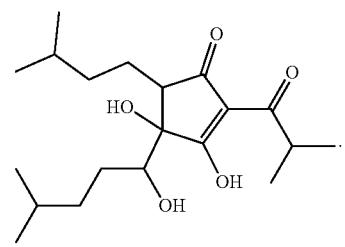
12. The compound of claim 4, wherein the compound has a structure selected from:
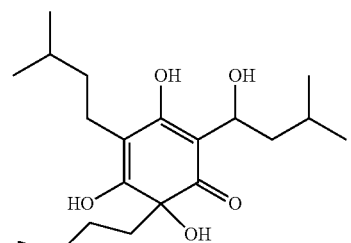
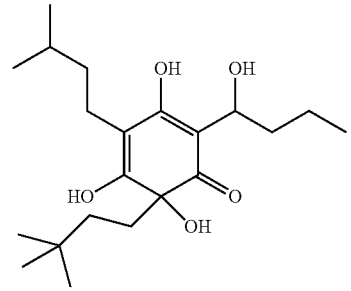

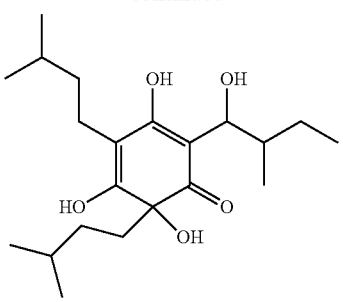
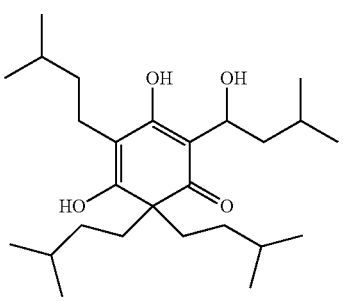
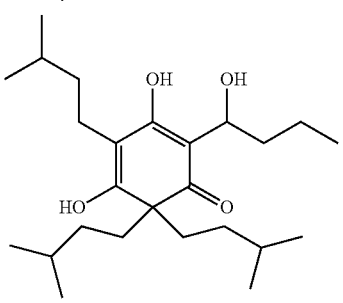
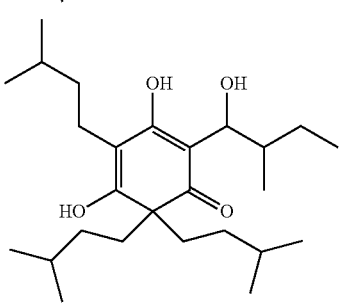
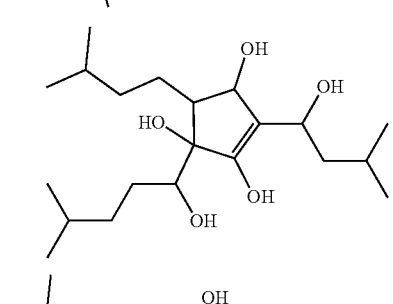
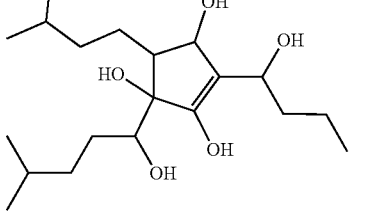
and
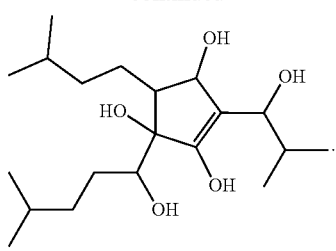
.
13. The compound of claim 4, wherein the compound has a structure selected from:
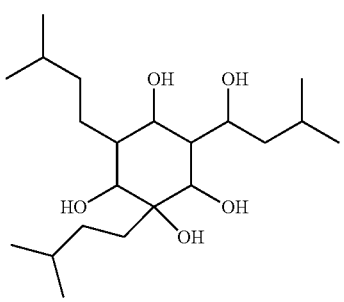
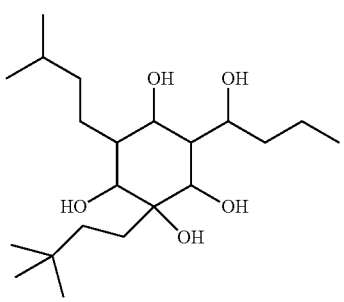
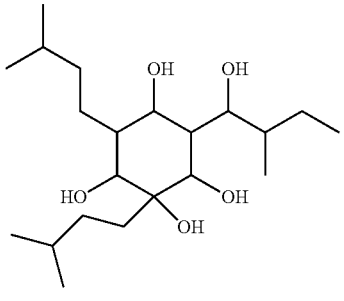
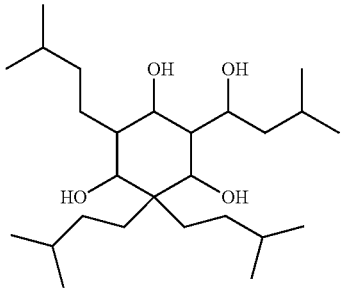

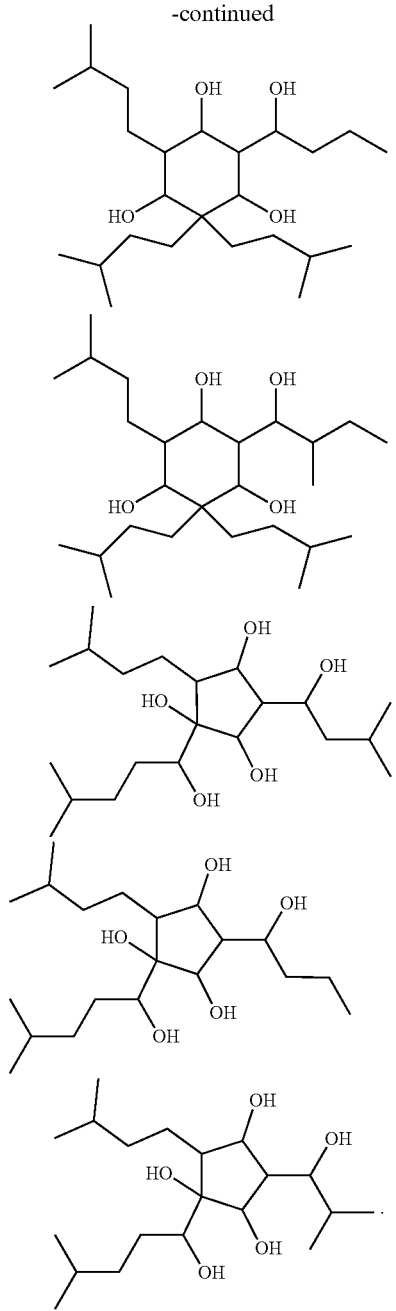
14. The compound of claim 4, wherein the compound is selected from:
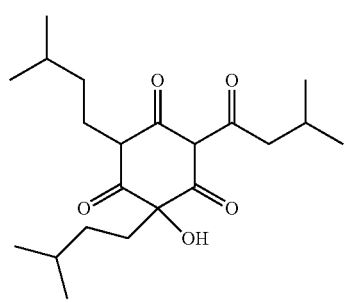
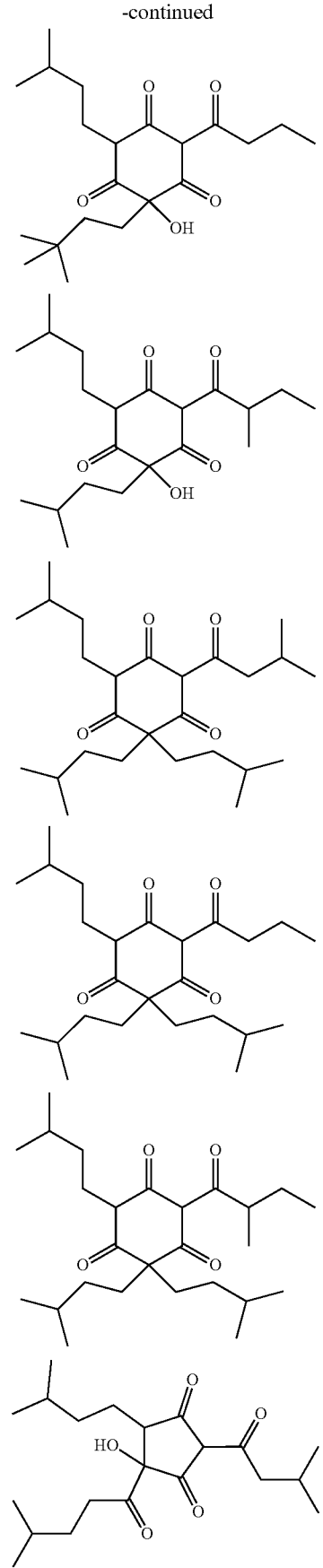

-continued

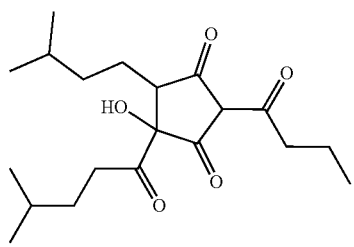

and

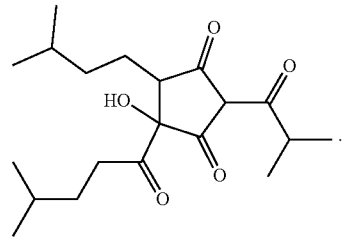

.

15. The compound of claim 4, wherein the compound has a structure selected from:

antiperspirant agents, antibacterial agents, antifungal agents, hydrocarbons, stabilizers, and viscosity controlling agents.

16. An emollient, solubilizer, anti-frizz agent, lubricant, carrier, conditioner, surfactant, adjuvant, dispersant, emulsifier, fuel, paraffin, candle, or precursor of a polymer, film-former, resin, or composite, comprising or consisting of a compound which is a hydrogenated derivative of a humulone, lupulone or isohumulone.

17. A composition comprising a compound according to claim 4, in admixture with one or more pharmaceutically acceptable, cosmetically acceptable, or industrially acceptable excipients or carriers, for example, selected from solvents, oils, surfactants, emollients, diluents, glidants, abrasives, humectants, polymers, plasticizers, catalysts, antioxidants, coloring agents, flavoring agents, fragrance agents, -continued

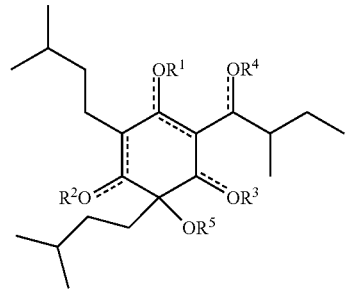

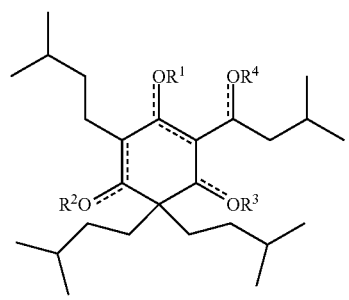

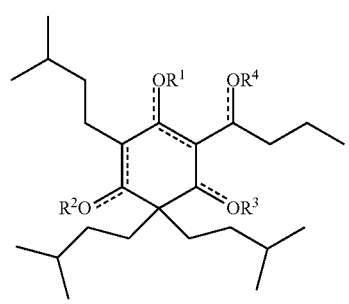

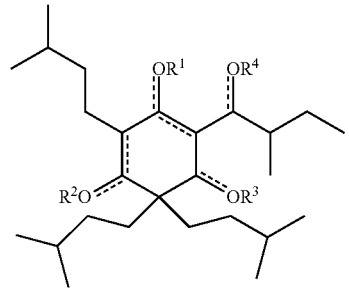

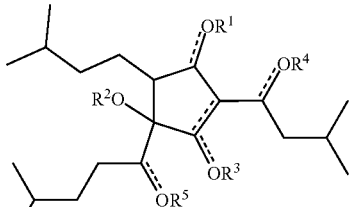

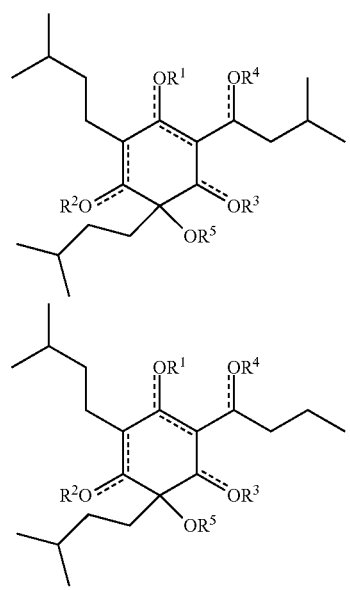

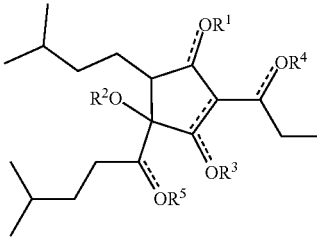

and

-continued

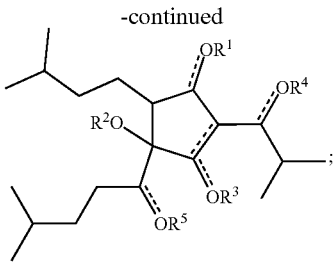

wherein $R^1$, $R^2$, $R^3$, $R^4$, and $R^5$ are each as defined in claim 4.

18. An emollient, solubilizer, anti-frizz agent, lubricant, carrier, conditioner, surfactant, adjuvant, dispersant, emulsifier, fuel, paraffin, candle, or precursor of a polymer, film-former, resin, or composite, comprising or consisting of a compound according to claim 4.

19. The composition according to claim 1, wherein the composition is a cosmetic composition, sunscreen composition, plastic composition, lubricant composition, personal care composition, cleaning composition, or air freshener.

20. The composition according to claim 19, wherein the composition is a soap, skin cream or lotion, balm, shampoo, body wash, hydrating cream, deodorant, antiperspirant, after-shave lotion, cologne, perfume, other hair care or skin care product, surface cleaner, metal cleaner, wood cleaner, glass cleaner, body cleaner, dish-washing detergent, or laundry detergent.

21. The composition according to claim 17, wherein the composition is a cosmetic composition, sunscreen composition, plastic composition, lubricant composition, personal care composition, cleaning composition, or air freshener.

22. The composition according to claim 21, wherein the composition is a soap, skin cream or lotion, balm, shampoo, body wash, hydrating cream, deodorant, antiperspirant, after-shave lotion, cologne, perfume, other hair care or skin care product, surface cleaner, metal cleaner, wood cleaner, glass cleaner, body cleaner, dish-washing detergent, or laundry detergent.

* * * * *

UNITED STATES PATENT AND TRADEMARK OFFICE
CERTIFICATE OF CORRECTION

PATENT NO. : 12,098,120 B2
APPLICATION NO. : 17/820861
DATED : September 24, 2024
INVENTOR(S) : Patrick Foley Page 1 of 7

It is certified that error appears in the above-identified patent and that said Letters Patent is hereby corrected as shown below:

In the Specification

Column 12, Line 35 to Line 50, the following structure

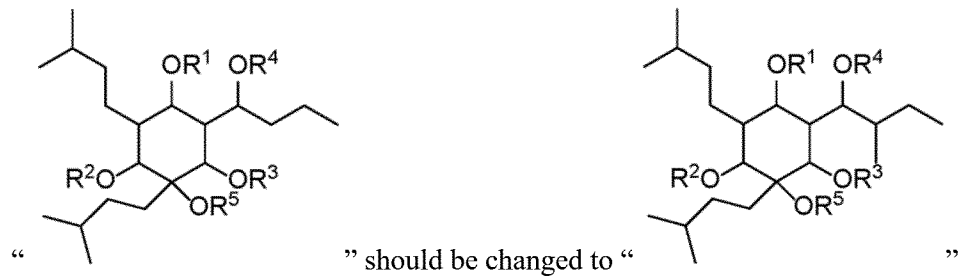

" should be changed to "                    "

Column 16, Line 35 to Line 45, the following structure

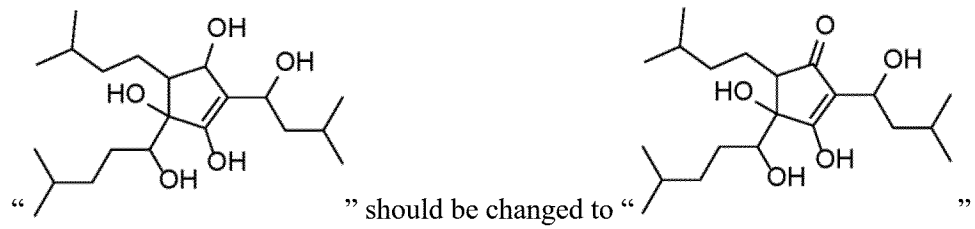

" should be changed to "                    "

Column 16, Line 45 to Line 55, the following structure

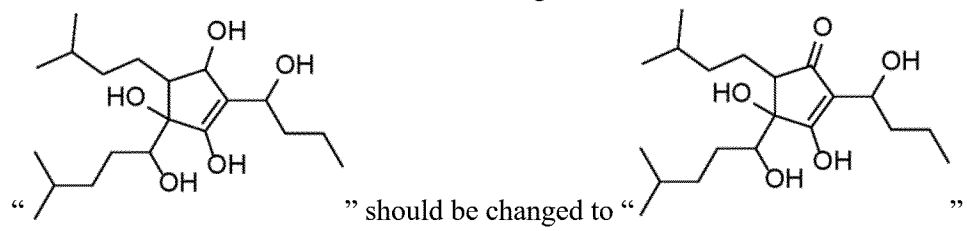

" should be changed to "                    "

Signed and Sealed this
Tenth Day of December, 2024

Katherine Kelly Vidal
*Director of the United States Patent and Trademark Office*

CERTIFICATE OF CORRECTION (continued)
U.S. Pat. No. 12,098,120 B2

Column 16, Line 55 to Line 65, the following structure

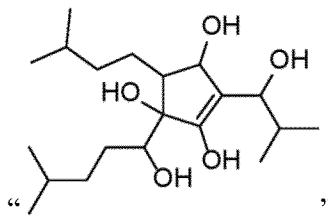 " should be changed to " 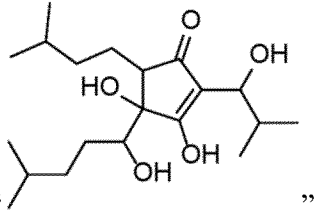 "

Column 18, Line 15 to Line 25, the following structure

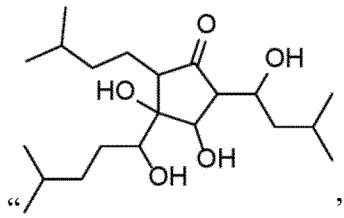 " should be changed to " 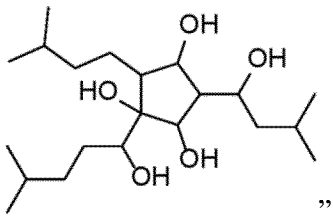 "

Column 18, Line 25 to Line 40, the following structure

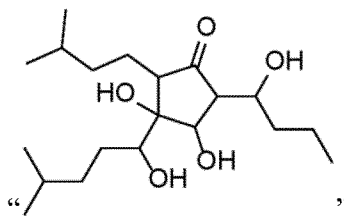 " should be changed to " 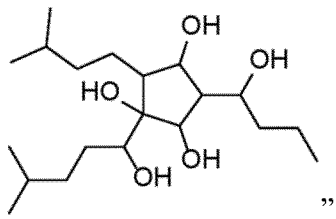 "

Column 18, Line 40 to Line 50, the following structure

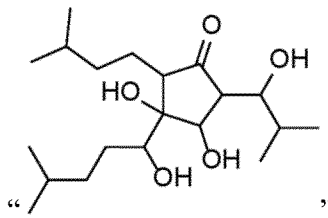 " should be changed to " 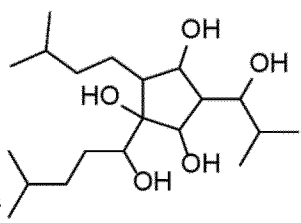 "

Column 19, Line 45 to Line 55, the following structure

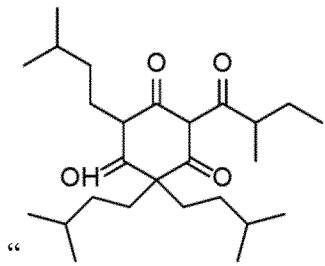 " should be changed to "  "

Column 19, Line 55 to Line 65, the following structure

" 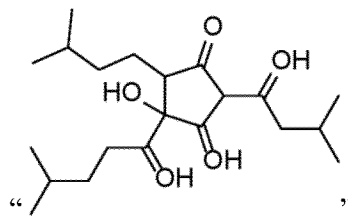 " should be changed to " 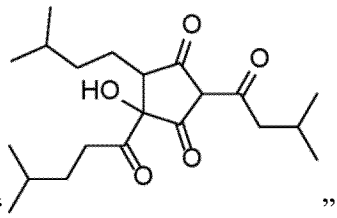 "

Column 20, Line 1 to Line 10, the following structure

" 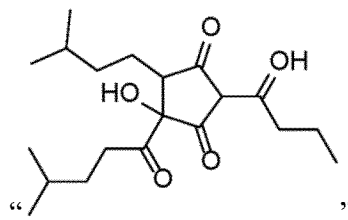 " should be changed to " 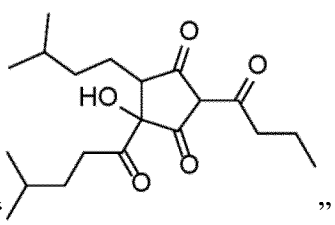 "

Column 20, Line 15 to Line 25, the following structure

" 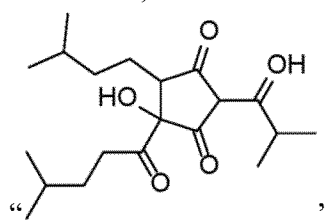 " should be changed to " 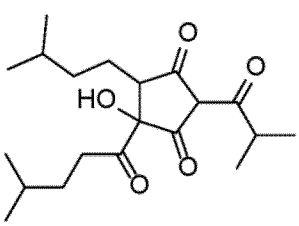 "

Column 24, Line 53 to Line 65, the following structure

" 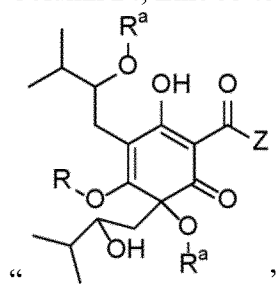 " should be changed to " 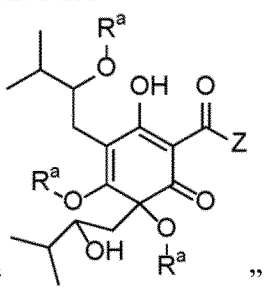 "

In the Claims

Column 34, Line 25 to Line 35, Claim 4, the following structure

" 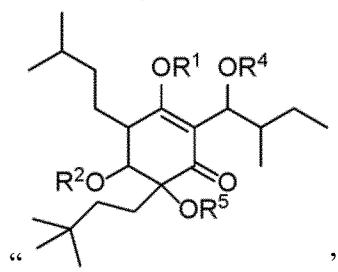 " should be changed to " 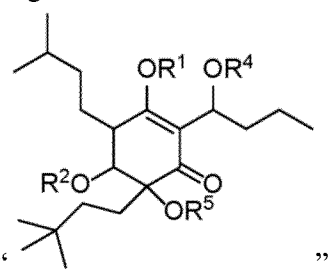 "

CERTIFICATE OF CORRECTION (continued)
U.S. Pat. No. 12,098,120 B2

Column 35, Line 55, Claim 4, after the fifth structure in the column and before the sixth structure in the column, insert the following structure -- 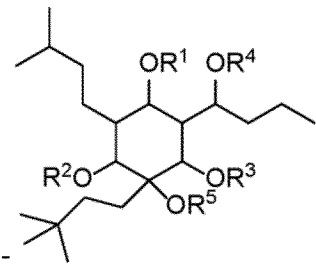 --

Column 37, Line 11-12, Claim 4, "–C(O)–C$_{1-21}$alkyl-SO$_{20}$C$_{1-6}$alkyl" should be changed to "–C(O)–C$_{1-21}$alkyl-SO$_2$OC$_{1-6}$alkyl"

Column 38, Line 25 to Line 35, Claim 5, the following structure 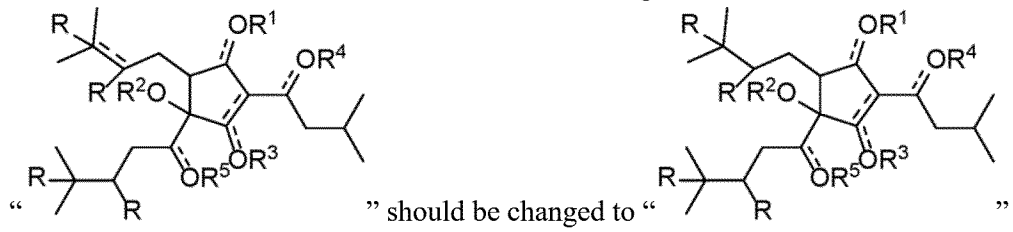

Column 39, Line 8, Claim 5, "each === is either" should be changed to "each - - - is either"

Column 39, Line 10, Claim 5, "bonds === and === are" should be changed to "bonds === and - - - are"

Column 39, Line 20 to Column 40, Line 50, Claim 6, the nine structures shown should be deleted and replaced by the following nine structures:

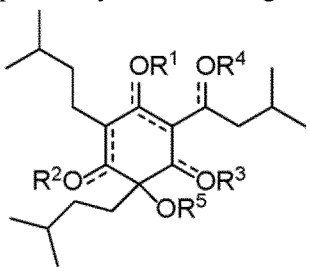 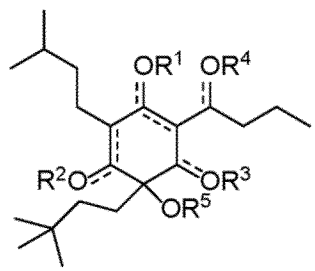 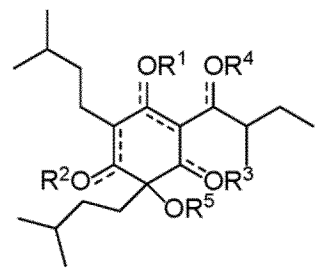

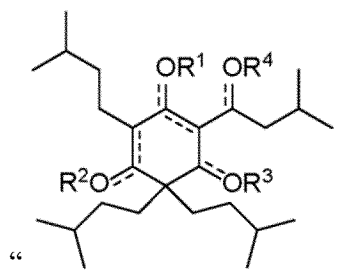 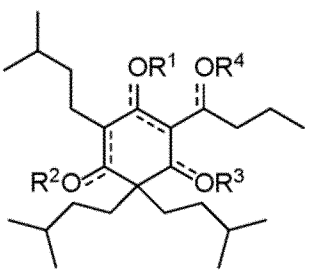 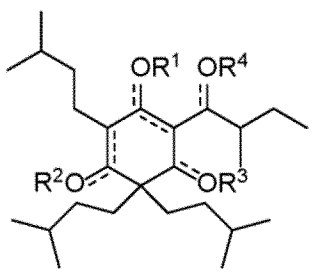

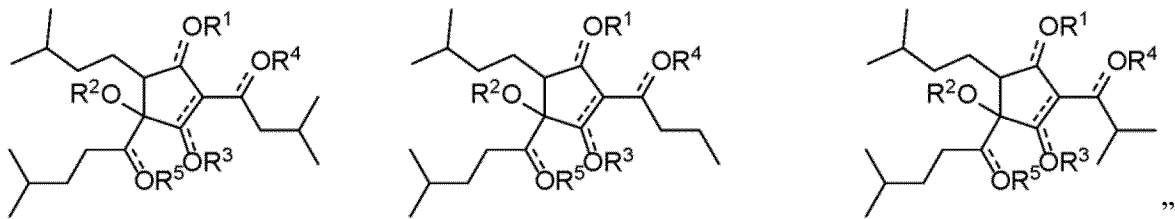

Column 41, Line 7, Claim 6, "each === is either" should be changed to "each --- is either"

Column 41, Line 9, Claim 6, "bonds === and === are" should be changed to "bonds === and --- are"

Column 46, Line 10 to Line 20, Claim 9, the following structure

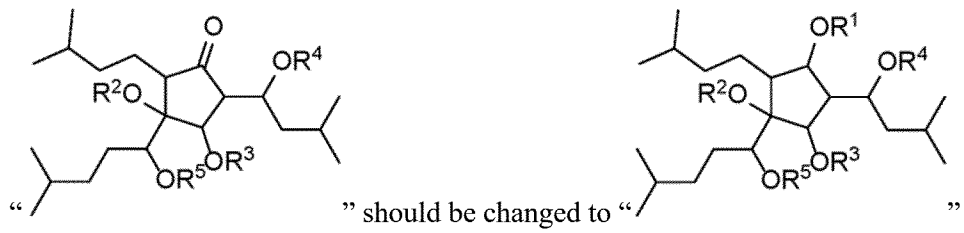

" should be changed to " "

Column 46, Line 20 to Line 30, Claim 9, the following structure

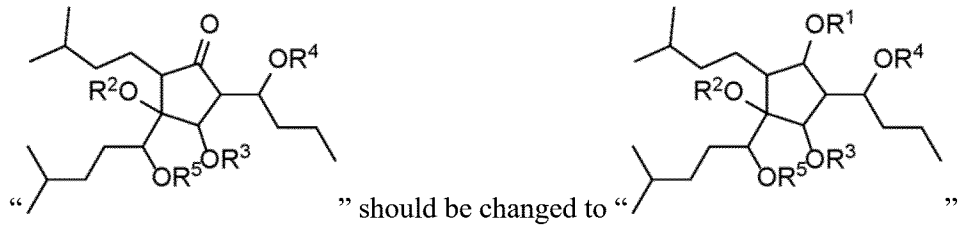

" should be changed to " "

Column 46, Line 30 to Line 40, Claim 9, the following structure

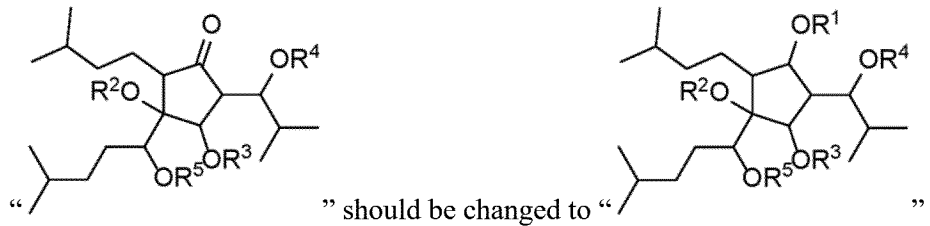

" should be changed to " "

Column 49, Line 50 to Line 58, Claim 12, the following structure

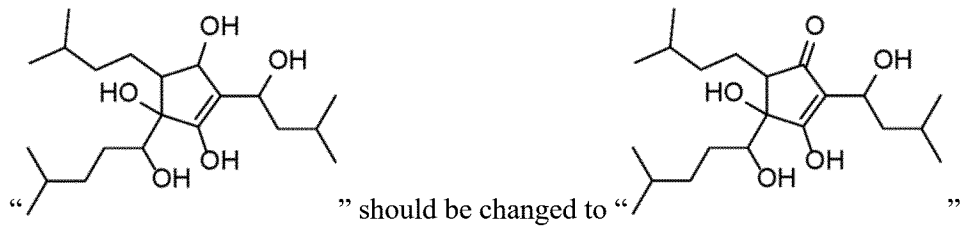

" should be changed to " "

Column 49, Line 58 to Line 65, Claim 12, the following structure

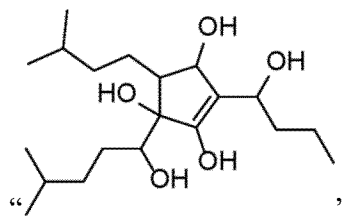 " should be changed to " 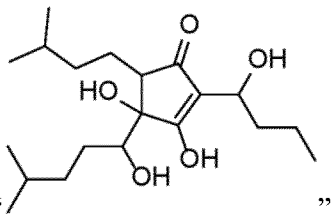 "

Column 50, Line 1 to Line 10, Claim 12, the following structure

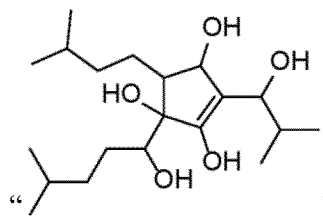 " should be changed to " 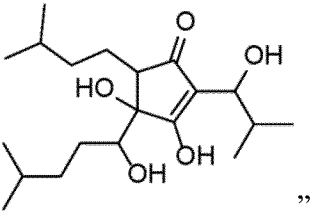 "

Column 53, Line 24-27, Claim 15, "antiperspirant agents, antibacterial agents, antifungal agents, hydrocarbons, stabilizers, and viscosity control agents" should be deleted and replaced with the following nine structures:

" 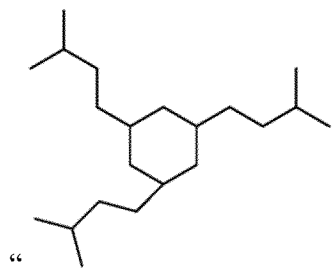 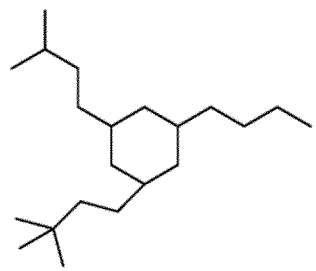 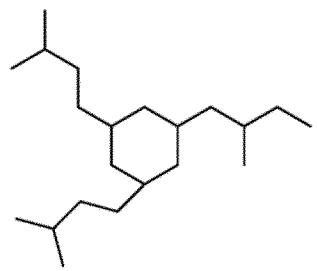

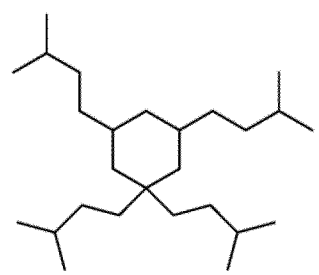 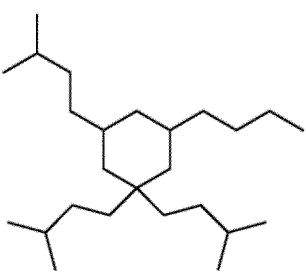 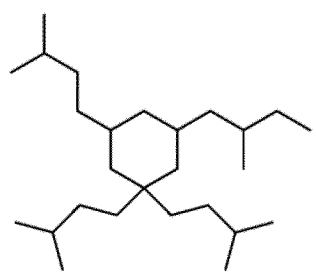

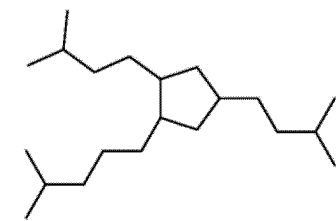 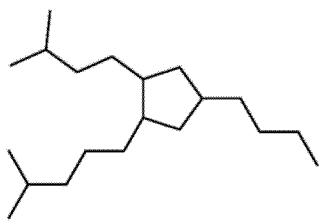 and 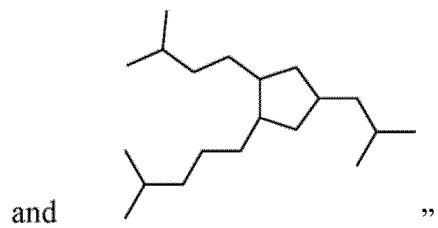 "

CERTIFICATE OF CORRECTION (continued)
U.S. Pat. No. 12,098,120 B2

Column 53, Line 38, Claim 17, "or carriers, for example, selected from" should be changed to "or carriers selected from"

Column 53, Line 42 to Column 55, Line 14, Claim 17, the recitation beginning with "fragrance agents," followed by nine chemical structures and through "are each as defined in claim 4." should be deleted and replaced with "fragrance agents, antiperspirant agents, antibacterial agents, antifungal agents, hydrocarbons, stabilizers, and viscosity control agents."